United States Patent [19]
Londos et al.

[11] Patent Number: 6,074,842
[45] Date of Patent: Jun. 13, 2000

[54] CLONING OF PERILIPIN PROTEINS

[75] Inventors: Constantine Londos, Garrett Park, Md.; Andrew S. Greenberg, Newton Centre, Mass.; Alan R. Kimmel, Ashton, Md.; John J. Egan, Mountain Lakes, N.J.

[73] Assignee: The United States of America as represented by the Department of Health and Human Services

[21] Appl. No.: 08/767,579

[22] Filed: Dec. 16, 1996

Related U.S. Application Data

[60] Division of application No. 08/132,649, Oct. 4, 1993, Pat. No. 5,585,462, which is a continuation-in-part of application No. 07/712,152, Jun. 11, 1991, abandoned.

[51] Int. Cl.[7] .................... C12N 15/63; C12N 15/09; C12N 5/10; C12N 15/00
[52] U.S. Cl. .............. 435/69.1; 435/172.3; 435/320.1; 435/325; 435/363; 435/366; 536/23.1; 536/23.5
[58] Field of Search ............... 435/172.3, 320.1, 435/325, 252.3, 353, 363, 366, 69.1; 536/23.1, 23.5; 935/9, 22, 23, 33, 66, 70

[56] References Cited

U.S. PATENT DOCUMENTS 4,675,285  6/1987  Clark et al. .................... 435/6
5,585,462  12/1996  Londos et al. .................... 530/350

FOREIGN PATENT DOCUMENTS

92/22638  12/1992  WIPO .

OTHER PUBLICATIONS

Kimmel et al. (Jan. 18–25, 1991) J. Cell. Biochem. Suppl 15B, p. 31, abstract CA309.
Greenberg et al. (May 1991) Clinical Research abstract.
Maruyama et al. (1986) Nuc. Acids Res 14: r151–r197.
Webster's II New Riverside University Dictionary, Soukhanov et al. (eds.) 1984, Houghton Mifflin Company, Boston, MA, p. 67.

*Primary Examiner*—Karen M. Hauda
*Attorney, Agent, or Firm*—Townsend & Townsend & Crew LLP

[57] ABSTRACT

The present invention provides isolated nucleic acid sequences, i.e., polynucleotides, which encode a family of perilipin proteins. The present invention also provides isolated, substantially purified perilipin proteins which are useful as markers for differentiating true adipocytes from non-adipocyte cells which, as a result of pathophysiological conditions, assume adipocyte characteristics and become lipid-laden. The present invention further provides methods for producing a substantially purified perilipin protein and methods for detecting the presence of such perilipin proteins in a biological samples.

14 Claims, 12 Drawing Sheets

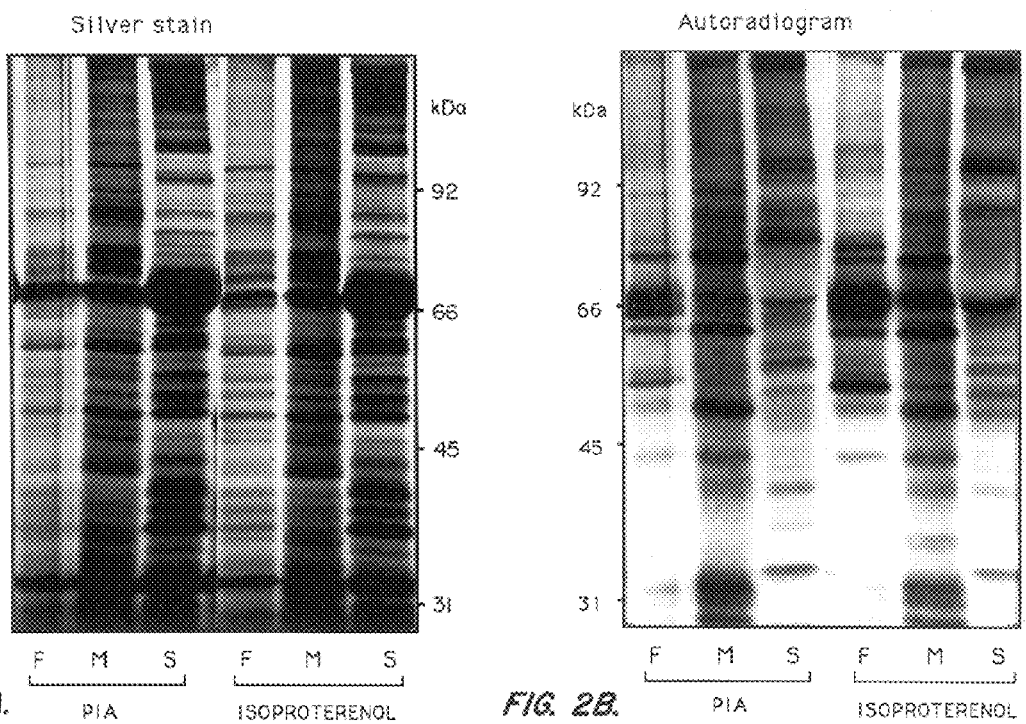

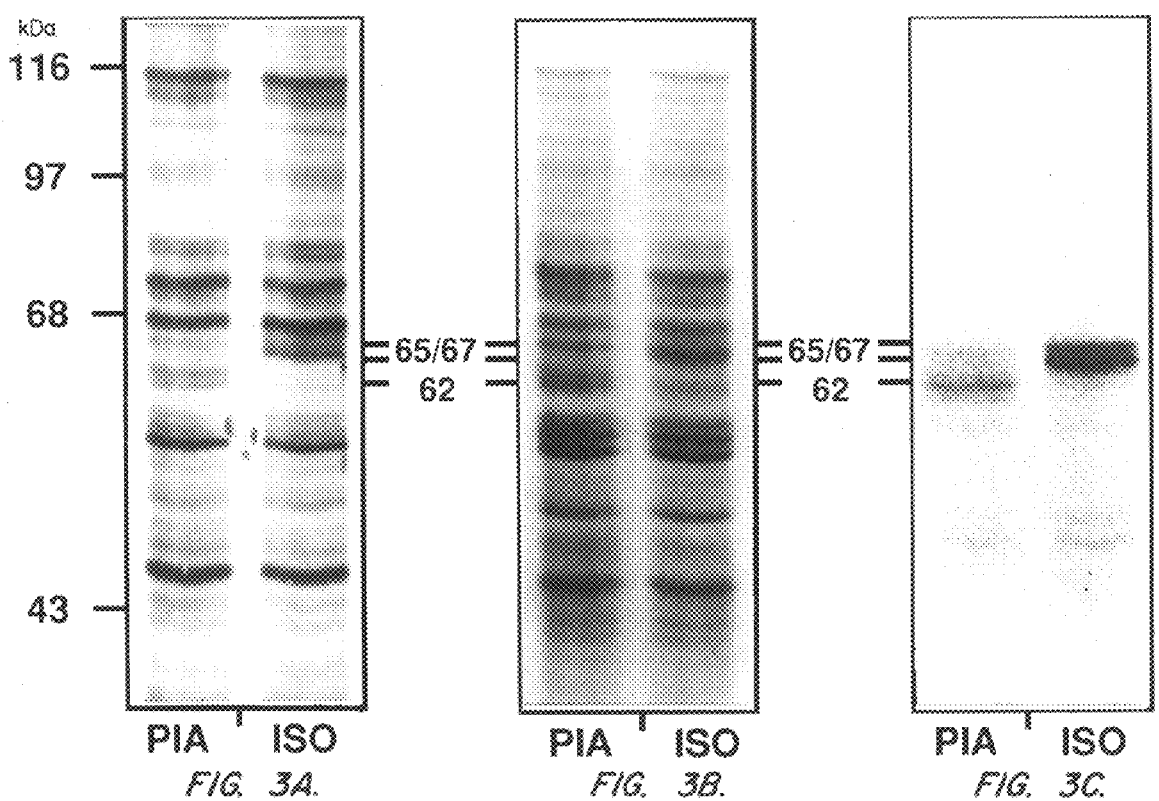

0   2.5   5.0   10   20   0   0   2.5   5.0   10   20

Alkaline phosphatase (Units x 10)

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 2080 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: RAT (ix) FEATURE:
        (A) NAME/KEY: misc_feature
        (B) LOCATION: 1..2080

(D) OTHER INFORMATION: /standard_name= "NSEQOFA.RAT"
  /note= "Nucleotide sequence of RAT perilipin "A"
  cDNA"

(ix) FEATURE:
  (A) NAME/KEY: CDS
  (B) LOCATION: 88..1638

(xi) SEQUENCE DESCRIPTION: SEQ ID NO:1:

```
GTGAGAGGTA GGGAGGGAAC CCATGGAATA CAAGCCTGCC GGCTTCTGAT GGATCTGGGA      60

TTCTGCTTTG CAGCGTGAAG AGTAAGG ATG TCC ATG AAC AAG GGC CCG ACC         111
                             Met Ser Met Asn Lys Gly Pro Thr
                               1               5

CTG CTG GAT GGA GAC CTC CCT GAA CAG GAG AAT GTG CTC CAG AGA GTC       159
Leu Leu Asp Gly Asp Leu Pro Glu Gln Glu Asn Val Leu Gln Arg Val
 10              15                  20

CTG CAG CTG CCT GTG GTG AGC GGG ACC TGT GAG TGC TTC CAG AAG ACC       207
Leu Gln Leu Pro Val Val Ser Gly Thr Cys Glu Cys Phe Gln Lys Thr
 25              30                  35                  40

TAT AAC AGC ACC AAA GAA GCC CAC CCC CTG GTG GCC TCT GTG TGC AAT       255
Tyr Asn Ser Thr Lys Glu Ala His Pro Leu Val Ala Ser Val Cys Asn
             45                  50                  55

GCC TAT GAG AAG GGT GTA CAG GGT GCC AGC AAC CTG GCT GCC TGG AGC       303
Ala Tyr Glu Lys Gly Val Gln Gly Ala Ser Asn Leu Ala Ala Trp Ser
         60                  65                  70

ATG GAG CCG GTG GTC CGC CGG CTC TCC ACC CAG TTC ACA GCT GCT AAT       351
Met Glu Pro Val Val Arg Arg Leu Ser Thr Gln Phe Thr Ala Ala Asn
     75                  80                  85

GAG TTG GCC TGC AGA GGC CTG GAC CAC CTG GAG GAA AAG ATC CCG GCT       399
Glu Leu Ala Cys Arg Gly Leu Asp His Leu Glu Glu Lys Ile Pro Ala
 90                  95                 100

CTT CAA TAC CCT CCG GAA AAG ATC GCC TCT GAA CTG AAG GGC ACC ATC       447
Leu Gln Tyr Pro Pro Glu Lys Ile Ala Ser Glu Leu Lys Gly Thr Ile
105                 110                 115                 120

TCT ACC CGC CTC CGA AGC GCC AGG AAC AGC ATC AGC GTG CCC ATT GCA       495
Ser Thr Arg Leu Arg Ser Ala Arg Asn Ser Ile Ser Val Pro Ile Ala
                125                 130                 135

AGC ACT TCT GAC AAG GTT CTG GGG GCC ACT CTG GCC GGC TGT GAG CTT       543
Ser Thr Ser Asp Lys Val Leu Gly Ala Thr Leu Ala Gly Cys Glu Leu
            140                 145                 150

GCC TTG GGG ATG GCC AAG GAG ACA GCG GAA TAT GCT GCC AAC ACC CGA       591
Ala Leu Gly Met Ala Lys Glu Thr Ala Glu Tyr Ala Ala Asn Thr Arg
        155                 160                 165

GTT GGC CGA CTG GCC TCT GGA GGG GCT GAT CTG GCT TTG GGA AGC ATC       639
Val Gly Arg Leu Ala Ser Gly Gly Ala Asp Leu Ala Leu Gly Ser Ile
    170                 175                 180

GAG AAG GTG GTA GAA TAT CTC CTG CCA CCA GAC AAG GTG GAG TCA GCC       687
Glu Lys Val Val Glu Tyr Leu Leu Pro Pro Asp Lys Val Glu Ser Ala
185                 190                 195                 200

CCT TCT TCA GGA CGG CAA AAG ACG CAG AAG GCT CCC AAG GCC AAA CCA       735
Pro Ser Ser Gly Arg Gln Lys Thr Gln Lys Ala Pro Lys Ala Lys Pro
                205                 210                 215

AGC CTT TTG AGG AGG GTC AGC ACC CTG GCC AAC ACT CTT TCT CGA CAC       783
Ser Leu Leu Arg Arg Val Ser Thr Leu Ala Asn Thr Leu Ser Arg His
            220                 225                 230

ACC ATG CAG ACC ACA GCA CGG GCC CTG AAG CGG GGT CAC TCT CTG GCC       831
Thr Met Gln Thr Thr Ala Arg Ala Leu Lys Arg Gly His Ser Leu Ala
        235                 240                 245

ATG TGG ATC CCG GGT GTG GCA CCC CTG AGC AGC CTG GCC CAG TGG GGT       879
Met Trp Ile Pro Gly Val Ala Pro Leu Ser Ser Leu Ala Gln Trp Gly
    250                 255                 260
```

```
GCA TCG GCA GCC ATG CAG GTG GTG TCC CGG CGG CAG AGT GAG GTA CGG      927
Ala Ser Ala Ala Met Gln Val Val Ser Arg Arg Gln Ser Glu Val Arg
265                 270                 275                 280

GTG CCC TGG TTG CAC AAC CTG GCA GCC TCC AAG GAT GAG AAC CAT GAA      975
Val Pro Trp Leu His Asn Leu Ala Ala Ser Lys Asp Glu Asn His Glu
            285                 290                 295

GAC CAG ACA GAC ACA GAG GGA GAG GAG ACA GAT GAG GAG GAA GAA GAA     1023
Asp Gln Thr Asp Thr Glu Gly Glu Glu Thr Asp Glu Glu Glu Glu Glu
                300                 305                 310

GAA GAG TCA GAG GCC GAG GAG AAC GTG CTC AGA GAG GTA ACA GCC CTG     1071
Glu Glu Ser Glu Ala Glu Glu Asn Val Leu Arg Glu Val Thr Ala Leu
            315                 320                 325

CCC ACC CCT CTC GGC TTC CTG GGT GGT GTG GTA CAC ACC GTG CAG AAG     1119
Pro Thr Pro Leu Gly Phe Leu Gly Gly Val Val His Thr Val Gln Lys
330                 335                 340

ACT CTG CAG AAC ACC ATC TCG GCG GTG ACA TGG GCA CCT GCG GCT GTG     1167
Thr Leu Gln Asn Thr Ile Ser Ala Val Thr Trp Ala Pro Ala Ala Val
345                 350                 355                 360

CTG GGC ACG GTG GGA AGG ATC CTA CAC CTC ACA CCA GCC CAG GCT GTC     1215
Leu Gly Thr Val Gly Arg Ile Leu His Leu Thr Pro Ala Gln Ala Val
            365                 370                 375

TCC TCC ACC AAA GGG AGG GCC ATG TCC CTA TCC GAT GCC CTG AAG GGT     1263
Ser Ser Thr Lys Gly Arg Ala Met Ser Leu Ser Asp Ala Leu Lys Gly
                380                 385                 390

GTT ACG GAT AAC GTG GTA GAC ACT GTG GTA CAC TAT GTC CCG CTT CCC     1311
Val Thr Asp Asn Val Val Asp Thr Val Val His Tyr Val Pro Leu Pro
            395                 400                 405

AGG CTG TCC CTG ATG GAG CCC GAG AGC GAA TTC CAA GAC ATC GAT AAT     1359
Arg Leu Ser Leu Met Glu Pro Glu Ser Glu Phe Gln Asp Ile Asp Asn
410                 415                 420

CCT CCA GCA GAG GTG GAG CGC AAA GGG TCG GGG TCG CGG CCC GCC AGC     1407
Pro Pro Ala Glu Val Glu Arg Lys Gly Ser Gly Ser Arg Pro Ala Ser
425                 430                 435                 440

CCA GAG TCC ACG GCG CGC CCG GGC CAG CCC CGC GCA GCT TGC GCA GTG     1455
Pro Glu Ser Thr Ala Arg Pro Gly Gln Pro Arg Ala Ala Cys Ala Val
            445                 450                 455

CGG GGT CTC AGC GCG CCC TCT TGC CCC GAT CTG GAT GAC AAA ACC GAG     1503
Arg Gly Leu Ser Ala Pro Ser Cys Pro Asp Leu Asp Asp Lys Thr Glu
                460                 465                 470

ACA TCA GCG CGT CCT GGC CTC CTG GCT ATG CCC AGA GAG AAG CCT GCG     1551
Thr Ser Ala Arg Pro Gly Leu Leu Ala Met Pro Arg Glu Lys Pro Ala
            475                 480                 485

CGC AGG GTC AGC GAC AGC TTC TTC CGG CCC AGC GTC ATG GAG CCC ATC     1599
Arg Arg Val Ser Asp Ser Phe Phe Arg Pro Ser Val Met Glu Pro Ile
490                 495                 500

CTG GGC CGC ACG CAG TAC AGC CAG CTG CGC AAG AAG AGC TGAGTAGCCT      1648
Leu Gly Arg Thr Gln Tyr Ser Gln Leu Arg Lys Lys Ser
505                 510                 515

GCGCCCCTAA CCGCCCTGGC GCCACCCTCA CCGGAAGTCG CTTCTCTCCC CAAGGAAACA   1708

GAAACCACAC TTCCAAGTGG GCCACTCCTT CAGGTTGGCC TCTTGGGAGC CCGAGTCACA   1768

ACCCCACGAT GTTCTCGAGA CCCACATCAT TTCTAAGGCA TCCTTGGGGC TTGACCATCA   1828

CAGTCAGGTT TTAAGGGGCA CCGAGCGGCT GTCGACTCTT TCCTCTCTCG TGGGCTGAAT   1888

CTCTCATGGC TTTTTTTTTT TTTTTTTTTT AACTATAAAA GCAATTGCTT AATTGGATTT   1948

CTCACTTCTT TAACAAAACT TGGCCTGACT AGTTCTAAAA ATGTAGATCC CTTCTCTGTC   2008

GACACGTATT TATTGCCAAA AAGTAGTGCG TCAGTTGACT GTTTTCTCTT TCTTTTCTCT   2068
```

TGTTTTTCTC CT                                                                 2080

(2) INFORMATION FOR SEQ ID NO:2:

(i) SEQUENCE CHARACTERISTICS:
       (A) LENGTH: 517 amino acids
       (B) TYPE: amino acid
       (D) TOPOLOGY: linear (ii) MOLECULE TYPE: protein (xi) SEQUENCE DESCRIPTION: SEQ ID NO:2:

Met Ser Met Asn Lys Gly Pro Thr Leu Leu Asp Gly Asp Leu Pro Glu
 1               5                  10                  15

Gln Glu Asn Val Leu Gln Arg Val Leu Gln Leu Pro Val Val Ser Gly
             20                  25                  30

Thr Cys Glu Cys Phe Gln Lys Thr Tyr Asn Ser Thr Lys Glu Ala His
         35                  40                  45

Pro Leu Val Ala Ser Val Cys Asn Ala Tyr Glu Lys Gly Val Gln Gly
     50                  55                  60

Ala Ser Asn Leu Ala Ala Trp Ser Met Glu Pro Val Val Arg Arg Leu
65                  70                  75                  80

Ser Thr Gln Phe Thr Ala Ala Asn Glu Leu Ala Cys Arg Gly Leu Asp
                 85                  90                  95

His Leu Glu Glu Lys Ile Pro Ala Leu Gln Tyr Pro Pro Glu Lys Ile
            100                 105                 110

Ala Ser Glu Leu Lys Gly Thr Ile Ser Thr Arg Leu Arg Ser Ala Arg
        115                 120                 125

Asn Ser Ile Ser Val Pro Ile Ala Ser Thr Ser Asp Lys Val Leu Gly
    130                 135                 140

Ala Thr Leu Ala Gly Cys Glu Leu Ala Leu Gly Met Ala Lys Glu Thr
145                 150                 155                 160

Ala Glu Tyr Ala Ala Asn Thr Arg Val Gly Arg Leu Ala Ser Gly Gly
                165                 170                 175

Ala Asp Leu Ala Leu Gly Ser Ile Glu Lys Val Val Glu Tyr Leu Leu
            180                 185                 190

Pro Pro Asp Lys Val Glu Ser Ala Pro Ser Ser Gly Arg Gln Lys Thr
        195                 200                 205

Gln Lys Ala Pro Lys Ala Lys Pro Ser Leu Leu Arg Arg Val Ser Thr
    210                 215                 220

Leu Ala Asn Thr Leu Ser Arg His Thr Met Gln Thr Thr Ala Arg Ala
225                 230                 235                 240

Leu Lys Arg Gly His Ser Leu Ala Met Trp Ile Pro Gly Val Ala Pro
                245                 250                 255

Leu Ser Ser Leu Ala Gln Trp Gly Ala Ser Ala Ala Met Gln Val Val
            260                 265                 270

Ser Arg Arg Gln Ser Glu Val Arg Val Pro Trp Leu His Asn Leu Ala
        275                 280                 285

Ala Ser Lys Asp Glu Asn His Glu Asp Gln Thr Asp Thr Glu Gly Glu
    290                 295                 300

Glu Thr Asp Glu Glu Glu Glu Glu Glu Ser Glu Ala Glu Glu Asn
305                 310                 315                 320

Val Leu Arg Glu Val Thr Ala Leu Pro Thr Pro Leu Gly Phe Leu Gly
                325                 330                 335

Gly Val Val His Thr Val Gln Lys Thr Leu Gln Asn Thr Ile Ser Ala
            340                 345                 350

```
Val Thr Trp Ala Pro Ala Ala Val Leu Gly Thr Val Gly Arg Ile Leu
            355                 360                 365

His Leu Thr Pro Ala Gln Ala Val Ser Ser Thr Lys Gly Arg Ala Met
            370                 375                 380

Ser Leu Ser Asp Ala Leu Lys Gly Val Thr Asp Asn Val Val Asp Thr
385                 390                 395                 400

Val Val His Tyr Val Pro Leu Pro Arg Leu Ser Leu Met Glu Pro Glu
                405                 410                 415

Ser Glu Phe Gln Asp Ile Asp Asn Pro Pro Ala Glu Val Glu Arg Lys
            420                 425                 430

Gly Ser Gly Ser Arg Pro Ala Ser Pro Glu Ser Thr Ala Arg Pro Gly
            435                 440                 445

Gln Pro Arg Ala Ala Cys Ala Val Arg Gly Leu Ser Ala Pro Ser Cys
        450                 455                 460

Pro Asp Leu Asp Asp Lys Thr Glu Thr Ser Ala Arg Pro Gly Leu Leu
465                 470                 475                 480

Ala Met Pro Arg Glu Lys Pro Ala Arg Arg Val Ser Asp Ser Phe Phe
                485                 490                 495

Arg Pro Ser Val Met Glu Pro Ile Leu Gly Arg Thr Gln Tyr Ser Gln
            500                 505                 510

Leu Arg Lys Lys Ser
            515
```

(2) INFORMATION FOR SEQ ID NO:3:

(i) SEQUENCE CHARACTERISTICS:
        (A) LENGTH: 1702 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: RAT (ix) FEATURE:
        (A) NAME/KEY: misc_feature
        (B) LOCATION: 1..1702
        (D) OTHER INFORMATION: /standard_name= "NSEQOFB.RAT"
           /note= "Nucleotide sequence of Perilipin "B"
           cDNA."

(ix) FEATURE:
        (A) NAME/KEY: CDS
        (B) LOCATION: 88..1353

(xi) SEQUENCE DESCRIPTION: SEQ ID NO:3:

```
GTGAGAGGTA GGGAGGGAAC CCATGGAATA CAAGCCTGCC GGCTTCTGAT GGATCTGGGA        60

TTCTGCTTTG CAGCGTGAAG AGTAAGG ATG TCC ATG AAC AAG GGC CCG ACC           111
                            Met Ser Met Asn Lys Gly Pro Thr
                              1               5

CTG CTG GAT GGA GAC CTC CCT GAA CAG GAG AAT GTG CTC CAG AGA GTC         159
Leu Leu Asp Gly Asp Leu Pro Glu Gln Glu Asn Val Leu Gln Arg Val
     10                  15                  20

CTG CAG CTG CCT GTG GTG AGC GGG ACC TGT GAG TGC TTC CAG AAG ACC         207
Leu Gln Leu Pro Val Val Ser Gly Thr Cys Glu Cys Phe Gln Lys Thr
 25                  30                  35                  40

TAT AAC AGC ACC AAA GAA GCC CAC CCC CTG GTG GCC TCT GTG TGC AAT         255
Tyr Asn Ser Thr Lys Glu Ala His Pro Leu Val Ala Ser Val Cys Asn
```

-continued

```
                      45                    50                    55
GCC TAT GAG AAG GGT GTA CAG GGT GCC AGC AAC CTG GCT GCC TGG AGC       303
Ala Tyr Glu Lys Gly Val Gln Gly Ala Ser Asn Leu Ala Ala Trp Ser
                 60                  65                  70

ATG GAG CCG GTG GTC CGC CGG CTC TCC ACC CAG TTC ACA GCT GCT AAT       351
Met Glu Pro Val Val Arg Arg Leu Ser Thr Gln Phe Thr Ala Ala Asn
             75                  80                  85

GAG TTG GCC TGC AGA GGC CTG GAC CAC CTG GAG GAA AAG ATC CCG GCT       399
Glu Leu Ala Cys Arg Gly Leu Asp His Leu Glu Glu Lys Ile Pro Ala
         90                  95                 100

CTT CAA TAC CCT CCG GAA AAG ATC GCC TCT GAA CTG AAG GGC ACC ATC       447
Leu Gln Tyr Pro Pro Glu Lys Ile Ala Ser Glu Leu Lys Gly Thr Ile
105                 110                 115                 120

TCT ACC CGC CTC CGA AGC GCC AGG AAC AGC ATC AGC GTG CCC ATT GCA       495
Ser Thr Arg Leu Arg Ser Ala Arg Asn Ser Ile Ser Val Pro Ile Ala
                125                 130                 135

AGC ACT TCT GAC AAG GTT CTG GGG GCC ACT CTG GCC GGC TGT GAG CTT       543
Ser Thr Ser Asp Lys Val Leu Gly Ala Thr Leu Ala Gly Cys Glu Leu
            140                 145                 150

GCC TTG GGG ATG GCC AAG GAG ACA GCG GAA TAT GCT GCC AAC ACC CGA       591
Ala Leu Gly Met Ala Lys Glu Thr Ala Glu Tyr Ala Ala Asn Thr Arg
        155                 160                 165

GTT GGC CGA CTG GCC TCT GGA GGG GCT GAT CTG GCT TTG GGA AGC ATC       639
Val Gly Arg Leu Ala Ser Gly Gly Ala Asp Leu Ala Leu Gly Ser Ile
    170                 175                 180

GAG AAG GTG GTA GAA TAT CTC CTG CCA CCA GAC AAG GTG GAG TCA GCC       687
Glu Lys Val Val Glu Tyr Leu Leu Pro Pro Asp Lys Val Glu Ser Ala
185                 190                 195                 200

CCT TCT TCA GGA CGG CAA AAG ACG CAG AAG GCT CCC AAG GCC AAA CCA       735
Pro Ser Ser Gly Arg Gln Lys Thr Gln Lys Ala Pro Lys Ala Lys Pro
                205                 210                 215

AGC CTT TTG AGG AGG GTC AGC ACC CTG GCC AAC ACT CTT TCT CGA CAC       783
Ser Leu Leu Arg Arg Val Ser Thr Leu Ala Asn Thr Leu Ser Arg His
            220                 225                 230

ACC ATG CAG ACC ACA GCA CGG GCC CTG AAG CGG GGT CAC TCT CTG GCC       831
Thr Met Gln Thr Thr Ala Arg Ala Leu Lys Arg Gly His Ser Leu Ala
        235                 240                 245

ATG TGG ATC CCG GGT GTG GCA CCC CTG AGC AGC CTG GCC CAG TGG GGT       879
Met Trp Ile Pro Gly Val Ala Pro Leu Ser Ser Leu Ala Gln Trp Gly
    250                 255                 260

GCA TCG GCA GCC ATG CAG GTG GTG TCC CGG CGG CAG AGT GAG GTA CGG       927
Ala Ser Ala Ala Met Gln Val Val Ser Arg Arg Gln Ser Glu Val Arg
265                 270                 275                 280

GTG CCC TGG TTG CAC AAC CTG GCA GCC TCC AAG GAT GAG AAC CAT GAA       975
Val Pro Trp Leu His Asn Leu Ala Ala Ser Lys Asp Glu Asn His Glu
                285                 290                 295

GAC CAG ACA GAC ACA GAG GGA GAG GAG ACA GAT GAG GAG GAA GAA GAA      1023
Asp Gln Thr Asp Thr Glu Gly Glu Glu Thr Asp Glu Glu Glu Glu Glu
            300                 305                 310

GAA GAG TCA GAG GCC GAG GAG AAC GTG CTC AGA GAG GTA ACA GCC CTG      1071
Glu Glu Ser Glu Ala Glu Glu Asn Val Leu Arg Glu Val Thr Ala Leu
        315                 320                 325

CCC ACC CCT CTC GGC TTC CTG GGT GGT GTG GTA CAC ACC GTG CAG AAG      1119
Pro Thr Pro Leu Gly Phe Leu Gly Gly Val Val His Thr Val Gln Lys
    330                 335                 340

ACT CTG CAG AAC ACC ATC TCG GCG GTG ACA TGG GCA CCT GCG GCT GTG      1167
Thr Leu Gln Asn Thr Ile Ser Ala Val Thr Trp Ala Pro Ala Ala Val
345                 350                 355                 360

CTG GGC ACG GTG GGA AGG ATC CTA CAC CTC ACA CCA GCC CAG GCT GTC      1215
```

```
Leu Gly Thr Val Gly Arg Ile Leu His Leu Thr Pro Ala Gln Ala Val
                365                 370                 375
TCC TCC ACC AAA GGG AGG GCC ATG TCC CTA TCC GAT GCC CTG AAG GGT    1263
Ser Ser Thr Lys Gly Arg Ala Met Ser Leu Ser Asp Ala Leu Lys Gly
                380                 385                 390
GTT ACG GAT AAC GTG GTA GAC ACT GTG GTA CAC TAT GTC CCG GTG AGT    1311
Val Thr Asp Asn Val Val Asp Thr Val Val His Tyr Val Pro Val Ser
                395                 400                 405
CCT GCC CCA GGG CCA CCT TCT GAC TCC CAA GGT AGA TTT GAC            1353
Pro Ala Pro Gly Pro Pro Ser Asp Ser Gln Gly Arg Phe Asp
        410                 415                 420

TGAAGGAGAT ATAGACCCCC TTTTATCCAG TCCCTGGGCC CAGAACCTTC TTATACACTG  1413

ATCTTCCCCA GCCCAAAGTG CAAATGTTCA CAGCCCTGAC CTCAGACCTC CCCTCTCCTA  1473

GCCCCTAGCC CCCACCCTCC GACTTGTGCC TCCCACTCGA TGATAGAATC ATTTGTGAGT  1533

CTCTAGTGGC TCAGACTCCG GCCTCAGATC CTGGAGGAAG GGCCTGGTAA ATTTACATGC  1593

CACTGTTCAA TAGGCTTTCA TGGCACCTTG AACAGCAGGC TATACATCTG GGACAGCAG  1653

CTGGCCCTAT GTCACCAACA GGGAAAAAAA AAAAAAAAT CAGACTTTT              1702

(2) INFORMATION FOR SEQ ID NO:4:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Met Asn Lys Gly Pro Thr Leu Leu Asp Gly Asp Leu Pro Glu
 1               5                  10                  15

Gln Glu Asn Val Leu Gln Arg Val Leu Gln Leu Pro Val Val Ser Gly
                20                  25                  30

Thr Cys Glu Cys Phe Gln Lys Thr Tyr Asn Ser Thr Lys Glu Ala His
            35                  40                  45

Pro Leu Val Ala Ser Val Cys Asn Ala Tyr Glu Lys Gly Val Gln Gly
        50                  55                  60

Ala Ser Asn Leu Ala Ala Trp Ser Met Glu Pro Val Val Arg Arg Leu
65                  70                  75                  80

Ser Thr Gln Phe Thr Ala Ala Asn Glu Leu Ala Cys Arg Gly Leu Asp
                85                  90                  95

His Leu Glu Glu Lys Ile Pro Ala Leu Gln Tyr Pro Pro Glu Lys Ile
            100                 105                 110

Ala Ser Glu Leu Lys Gly Thr Ile Ser Thr Arg Leu Arg Ser Ala Arg
        115                 120                 125

Asn Ser Ile Ser Val Pro Ile Ala Ser Thr Ser Asp Lys Val Leu Gly
    130                 135                 140

Ala Thr Leu Ala Gly Cys Glu Leu Ala Leu Gly Met Ala Lys Glu Thr
145                 150                 155                 160

Ala Glu Tyr Ala Ala Asn Thr Arg Val Gly Arg Leu Ala Ser Gly Gly
                165                 170                 175

Ala Asp Leu Ala Leu Gly Ser Ile Glu Lys Val Val Glu Tyr Leu Leu
            180                 185                 190

Pro Pro Asp Lys Val Glu Ser Ala Pro Ser Ser Gly Arg Gln Lys Thr
        195                 200                 205

Gln Lys Ala Pro Lys Ala Lys Pro Ser Leu Leu Arg Arg Val Ser Thr
```

```
                  210                 215                 220
Leu Ala Asn Thr Leu Ser Arg His Thr Met Gln Thr Thr Ala Arg Ala
225                 230                 235                 240

Leu Lys Arg Gly His Ser Leu Ala Met Trp Ile Pro Gly Val Ala Pro
                245                 250                 255

Leu Ser Ser Leu Ala Gln Trp Gly Ala Ser Ala Ala Met Gln Val Val
            260                 265                 270

Ser Arg Arg Gln Ser Glu Val Arg Val Pro Trp Leu His Asn Leu Ala
        275                 280                 285

Ala Ser Lys Asp Glu Asn His Glu Asp Gln Thr Asp Thr Glu Gly Glu
    290                 295                 300

Glu Thr Asp Glu Glu Glu Glu Glu Glu Ser Glu Ala Glu Glu Asn
305                 310                 315                 320

Val Leu Arg Glu Val Thr Ala Leu Pro Thr Pro Leu Gly Phe Leu Gly
                325                 330                 335

Gly Val Val His Thr Val Gln Lys Thr Leu Gln Asn Thr Ile Ser Ala
                340                 345                 350

Val Thr Trp Ala Pro Ala Ala Val Leu Gly Thr Val Gly Arg Ile Leu
            355                 360                 365

His Leu Thr Pro Ala Gln Ala Val Ser Ser Thr Lys Gly Arg Ala Met
370                 375                 380

Ser Leu Ser Asp Ala Leu Lys Gly Val Thr Asp Asn Val Val Asp Thr
385                 390                 395                 400

Val Val His Tyr Val Pro Val Ser Pro Ala Pro Gly Pro Pro Ser Asp
                405                 410                 415

Ser Gln Gly Arg Phe Asp
                420

(2) INFORMATION FOR SEQ ID NO:5:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Homo sapiens (ix) FEATURE:
        (A) NAME/KEY: misc_feature
        (B) LOCATION: 1..1265
        (D) OTHER INFORMATION: /standard_name= "HUPERI"
            /note= "Nucleotide sequence of human Perilipin
            cDNA."

(ix) FEATURE:
        (A) NAME/KEY: CDS
        (B) LOCATION: 3..1265

(xi) SEQUENCE DESCRIPTION: SEQ ID NO:5:

CG GCA GCC GGA GTG AGT GTT GGG GTC CTG GGG CAC CTG CCT TTG CTG        47
   Ala Ala Gly Val Ser Val Gly Val Leu Gly His Leu Pro Leu Leu
   1               5                  10                  15

GAT GGA GAC CTC CCT GAG CAG GAG AAT GTG CTG CAG CGG GTC CTG CAA       95
Asp Gly Asp Leu Pro Glu Gln Glu Asn Val Leu Gln Arg Val Leu Gln
                20                  25                  30

CTG CCG GTG GTG AGT GGC ACC TGC GAA TGC TTC AGA AAG ACC TAC ACC      143
```

-continued

```
                Leu Pro Val Val Ser Gly Thr Cys Glu Cys Phe Gln Lys Thr Tyr Thr
                             35                  40                  45

AGC ACT AAG GAA GCC CAC CCC CTG GTG GCC TCT GTG TGC AAT GCC TAT                 191
Ser Thr Lys Glu Ala His Pro Leu Val Ala Ser Val Cys Asn Ala Tyr
         50                  55                  60

GAG AAG GGC GTG CAG AGC GCC AGT AGC TTG GCT GCC TGG AGC ATG GAG                 239
Glu Lys Gly Val Gln Ser Ala Ser Ser Leu Ala Ala Trp Ser Met Glu
     65                  70                  75

CCG GTG GTC CGC AGG CTG TCC ACC CAG TTC ACA GCT GCC AAT GAG CTG                 287
Pro Val Val Arg Arg Leu Ser Thr Gln Phe Thr Ala Ala Asn Glu Leu
 80                  85                  90                  95

GCC TGC CGA GGC TTG GAC CAC CTG GAG GAA AAG ATC CCC GCC CTC CAG                 335
Ala Cys Arg Gly Leu Asp His Leu Glu Glu Lys Ile Pro Ala Leu Gln
                100                 105                 110

TAC CCC CCT GAA AAG ATT GCT TCT GAG CTG AAG GAC ACC ATC TCC ACC                 383
Tyr Pro Pro Glu Lys Ile Ala Ser Glu Leu Lys Asp Thr Ile Ser Thr
            115                 120                 125

CGC CTC CGC AGT GCC AGA AAC AGC ATC AGC GTT CCC ATC GCG AGC ACT                 431
Arg Leu Arg Ser Ala Arg Asn Ser Ile Ser Val Pro Ile Ala Ser Thr
        130                 135                 140

TCA GAC AAG GTC CTG GGG GCC GCT TTG GCC GGG TGC GAG CTT GCC TGG                 479
Ser Asp Lys Val Leu Gly Ala Ala Leu Ala Gly Cys Glu Leu Ala Trp
    145                 150                 155

GGG GTG GCC AGA GAC ACT GCG GAA TTT GCT GCC AAC ACT CGA GCT GGC                 527
Gly Val Ala Arg Asp Thr Ala Glu Phe Ala Ala Asn Thr Arg Ala Gly
160                 165                 170                 175

CGA CTG GCT TCT GGA GGG GCC GAC TTG GCC TTG GGC AGC ATT GAG AAG                 575
Arg Leu Ala Ser Gly Gly Ala Asp Leu Ala Leu Gly Ser Ile Glu Lys
                180                 185                 190

GTG GTG GAG TAC CTC CTC CCT GCA GAC AAG GAA GAG TCA GCC CCT GCT                 623
Val Val Glu Tyr Leu Leu Pro Ala Asp Lys Glu Glu Ser Ala Pro Ala
            195                 200                 205

CCT GGA CAC CAG CAA GCC CAG AAG TCT CCC AAG GCC AAG CCA AGC CTC                 671
Pro Gly His Gln Gln Ala Gln Lys Ser Pro Lys Ala Lys Pro Ser Leu
        210                 215                 220

TTG AGC AGG GTT GGG GCT CTG ACC AAC ACC CTC TCT CGA TAC ACC GTG                 719
Leu Ser Arg Val Gly Ala Leu Thr Asn Thr Leu Ser Arg Tyr Thr Val
    225                 230                 235

CAG ACC ATG GCC CGG GCC CTG GAG CAG GGC CAC ACC GTG GCC ATG TGG                 767
Gln Thr Met Ala Arg Ala Leu Glu Gln Gly His Thr Val Ala Met Trp
240                 245                 250                 255

ATC CCA GGC GTG GTG CCC CTG AGC AGC CTG GCC CAG TGG GGT GCC TCA                 815
Ile Pro Gly Val Val Pro Leu Ser Ser Leu Ala Gln Trp Gly Ala Ser
                260                 265                 270

GTG GCC ATG CAG GCG GTG TCC CGG CGG AGG AGC GAA GTG CGG GTA CCC                 863
Val Ala Met Gln Ala Val Ser Arg Arg Arg Ser Glu Val Arg Val Pro
            275                 280                 285

TGG CTG CAC AGC CTC GCA GCC GCC CAG GAG GAG GAT CAT GAG GAC CAG                 911
Trp Leu His Ser Leu Ala Ala Ala Gln Glu Glu Asp His Glu Asp Gln
        290                 295                 300

ACA GAC ACG GAG GGA GAG GAC ACG GAG GAG GAG GAA GAA TTG GAG ACT                 959
Thr Asp Thr Glu Gly Glu Asp Thr Glu Glu Glu Glu Glu Leu Glu Thr
    305                 310                 315

GAG GAG AAC AAG TTC AGT GAG GTA GCA GCC CTG CCA GGC CCT CGA GGC                 1007
Glu Glu Asn Lys Phe Ser Glu Val Ala Ala Leu Pro Gly Pro Arg Gly
320                 325                 330                 335

CTC CTG GGT GGT GTG GCA CAT ACC CTG CAG AAG ACC CTC CAG ACC ACC                 1055
Leu Leu Gly Gly Val Ala His Thr Leu Gln Lys Thr Leu Gln Thr Thr
                340                 345                 350
```

―continued

```
ATC TCG GCT GTG ACA TGG GCA CCT GCA GCT GTG CTG GGC ATG GCA GGG      1103
Ile Ser Ala Val Thr Trp Ala Pro Ala Ala Val Leu Gly Met Ala Gly
        355                 360                 365

AGG GTG CTG CAC CTC ACA CCA GCC CCT GCT GTC TCC TCA ACC AAG GGG      1151
Arg Val Leu His Leu Thr Pro Ala Pro Ala Val Ser Ser Thr Lys Gly
        370                 375                 380

AGG GCC ATG TCC CTA TCA GAT GCC CTG AAG GGC GTT ACT GAC AAC GTG      1199
Arg Ala Met Ser Leu Ser Asp Ala Leu Lys Gly Val Thr Asp Asn Val
385                 390                 395

GTG GAC ACA GTG GTG CAT TAC GTG CCG CTC CCC AGG CTG TCG CTG ATG      1247
Val Asp Thr Val Val His Tyr Val Pro Leu Pro Arg Leu Ser Leu Met
400                 405                 410                 415

GAG CCC GAG AGC GAA TTC                                               1265
Glu Pro Glu Ser Glu Phe
                420
```

(2) INFORMATION FOR SEQ ID NO:6:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO:6:

```
Ala Ala Gly Val Ser Val Gly Val Leu Gly His Leu Pro Leu Leu Asp
1               5                   10                  15

Gly Asp Leu Pro Glu Gln Glu Asn Val Leu Gln Arg Val Leu Gln Leu
                20                  25                  30

Pro Val Val Ser Gly Thr Cys Glu Cys Phe Gln Lys Thr Tyr Thr Ser
            35                  40                  45

Thr Lys Glu Ala His Pro Leu Val Ala Ser Val Cys Asn Ala Tyr Glu
        50                  55                  60

Lys Gly Val Gln Ser Ala Ser Ser Leu Ala Ala Trp Ser Met Glu Pro
65                  70                  75                  80

Val Val Arg Arg Leu Ser Thr Gln Phe Thr Ala Ala Asn Glu Leu Ala
                85                  90                  95

Cys Arg Gly Leu Asp His Leu Glu Glu Lys Ile Pro Ala Leu Gln Tyr
            100                 105                 110

Pro Pro Glu Lys Ile Ala Ser Glu Leu Lys Asp Thr Ile Ser Thr Arg
        115                 120                 125

Leu Arg Ser Ala Arg Asn Ser Ile Ser Val Pro Ile Ala Ser Thr Ser
130                 135                 140

Asp Lys Val Leu Gly Ala Ala Leu Ala Gly Cys Glu Leu Ala Trp Gly
145                 150                 155                 160

Val Ala Arg Asp Thr Ala Glu Phe Ala Ala Asn Thr Arg Ala Gly Arg
                165                 170                 175

Leu Ala Ser Gly Gly Ala Asp Leu Ala Leu Gly Ser Ile Glu Lys Val
            180                 185                 190

Val Glu Tyr Leu Leu Pro Ala Asp Lys Glu Glu Ser Ala Pro Ala Pro
        195                 200                 205

Gly His Gln Gln Ala Gln Lys Ser Pro Lys Ala Lys Pro Ser Leu Leu
    210                 215                 220

Ser Arg Val Gly Ala Leu Thr Asn Thr Leu Ser Arg Tyr Thr Val Gln
225                 230                 235                 240

Thr Met Ala Arg Ala Leu Glu Gln Gly His Thr Val Ala Met Trp Ile
                245                 250                 255
```

```
Pro Gly Val Val Pro Leu Ser Ser Leu Ala Gln Trp Gly Ala Ser Val
            260                 265                 270

Ala Met Gln Ala Val Ser Arg Arg Ser Glu Val Arg Val Pro Trp
            275                 280                 285

Leu His Ser Leu Ala Ala Ala Gln Glu Glu Asp His Glu Asp Gln Thr
            290                 295                 300

Asp Thr Glu Gly Glu Asp Thr Glu Glu Glu Glu Leu Glu Thr Glu
305                 310                 315                 320

Glu Asn Lys Phe Ser Glu Val Ala Ala Leu Pro Gly Pro Arg Gly Leu
            325                 330                 335

Leu Gly Gly Val Ala His Thr Leu Gln Lys Thr Leu Gln Thr Thr Ile
            340                 345                 350

Ser Ala Val Thr Trp Ala Pro Ala Ala Val Leu Gly Met Ala Gly Arg
            355                 360                 365

Val Leu His Leu Thr Pro Ala Pro Ala Val Ser Ser Thr Lys Gly Arg
            370                 375                 380

Ala Met Ser Leu Ser Asp Ala Leu Lys Gly Val Thr Asp Asn Val Val
385                 390                 395                 400

Asp Thr Val Val His Tyr Val Pro Leu Pro Arg Leu Ser Leu Met Glu
            405                 410                 415

Pro Glu Ser Glu Phe
            420

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: RAT (ix) FEATURE:
        (A) NAME/KEY: misc_feature
        (B) LOCATION: 1..24
        (D) OTHER INFORMATION: /note= "This sequence hybridizes
            specifically to rat perilipin A mRNA but not to
            rat perilipin B mRNA."

(xi) SEQUENCE DESCRIPTION: SEQ ID NO:7:

CACTATGTCC CGCTTCCCAG GCTG                                              24

(2) INFORMATION FOR SEQ ID NO:8:

(i) SEQUENCE CHARACTERISTICS:
        (A) LENGTH: 397 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: RAT (ix) FEATURE:
        (A) NAME/KEY: misc_feature
```

(B) LOCATION: 1..397
(D) OTHER INFORMATION: /note= "This sequence will only
    hybridize to rat perilipin B mRNA but not rat
    perilipin A mRNA."

(xi) SEQUENCE DESCRIPTION: SEQ ID NO:8:

GTAAGTCCTG CCCCAGGGCC ACCTTCTGAC TCCCAAGGTA GATTTGACTG AAGGAGATAT      60

AGACCCCCTT TTATCCAGTC CCTGGGCCCA GAACCTTCTT ATACACTGAT CTTCCCCAGC     120

CCAAAGTGCA AATGTTCACA GCCCTGACCT CAGACCTCCC CTCTCCTAGC CCCTAGCCCC     180

CACCCTCCGA CTTGTGCCTC CCACTCGATG ATAGAATCAT TTGTGAGTCT CTAGTGGCTC     240

AGACTCCGGC CTCAGATCCT GGAGGAAGGG CCTGGTAAAT TTACATGCCA CTGTTCAATA     300

GGCTTTCATG GCACCTTGAA CAGCAGGCTA TACATCTGGG ACAGCAGCT GGCCCTATGT      360

CACCAACAGG GAAAAAAAAA AAAAAAATCA GACTTTT                              397

(2) INFORMATION FOR SEQ ID NO:9:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Homo sapiens (ix) FEATURE:
        (A) NAME/KEY: misc_feature
        (B) LOCATION: 1..407
        (D) OTHER INFORMATION: /note= "3' human perilipin
            nucleotide sequences."

(xi) SEQUENCE DESCRIPTION: SEQ ID NO:9:

TACCCTGGCT GCACAGCCTC GCAGCCGCCC AGGAGGAGGA TCATGAGGAC CAGACAGACA      60

CGGAGGGAGA GGACACGGAG GAGGAGGAAG AATTGGAGAC TGAGGAGAAC AAGTTCAGTG     120

AGGTAGCAGC CCTGCCAGGC CCTCGAGGCC TCCTGGGTGG TGTGGCACAT ACCCTGCAGA     180

AGACCCTCCA GACCACCATC TCGGCTGTGA CATGGGCACC TGCAGCTGTG CTGGGCATGG     240

CAGGGAGGGT GCTGCACCTC ACACCAGCCC CTGCTGTCTC CTCAACCAAG GGAGGGCCA      300

TGTCCCTATC AGATGCCCTG AAGGGCGTTA CTGACAACGT GGTGGACACA GTGGTGCATT     360

ACGTGCCGCT CCCCAGGCTG TCGCTGATGG AGCCCGAGAG CGAATTC                   407

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Homo sapiens (ix) FEATURE:
        (A) NAME/KEY: misc_feature
        (B) LOCATION: 1..23
        (D) OTHER INFORMATION: /note= "Oligonucleotide probe -continued specific for human perilipin."

(xi) SEQUENCE DESCRIPTION: SEQ ID NO:10:

GAATTGGAGA CTGAGGAGAA CAA                    23

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: RAT (ix) FEATURE:
        (A) NAME/KEY: misc_feature
        (B) LOCATION: 1..32
        (D) OTHER INFORMATION: /note= "Oligonucleotide probe
            specific for rat perilipin."

(xi) SEQUENCE DESCRIPTION: SEQ ID NO:11:

GAAGAAGAAG AGTCAGAGGC CGAGGAGAAC GT                    32

CLONING OF PERILIPIN PROTEINS

This is a Division of application Ser. No. 08/132,649 filed Oct. 4, 1993, now allowed as U.S. Pat. No. 5,585,462, the disclosure of which is incorporated by reference which is a continuation-in-part application of U.S. patent application Ser. No. 07/712,152, filed Jun. 11, 1991 now abandoned.

FIELD OF THE INVENTION

The present invention relates, in general, to a family of perilipin proteins. More particularly, the present invention relates to DNA sequences encoding pertlipin; polypeptides encoded by such DNA sequences; recombinant DNA molecules containing DNA sequences encoding perilipin proteins; cells containing the recombinant DNA molecules; a method for producing perilipin proteins; a method for detecting perilipin proteins; and antibodies to the perilipin proteins.

BACKGROUND OF THE INVENTION

In higher organisms, the highly specialized adipocyte is the primary repository of energy, stored as triacylglycerol in the intracellular lipid droplet. Although the enzymes involved in both the formation and hydrolysis (i.e., lipolysis) of lipid are known, the molecular processes by which metabolites traffic in and out of the droplet remain a mystery. The elucidation of these processes is important for understanding not only how organisms regulate their daily energy needs, but also for understanding disorders of excessive abnormal lipid storage such as obesity or the severe depletion of energy reserves, such as occurs with the cachexia of chronic illness. Moreover, abnormal lipid depositions have been identified in a number of pathophysiological conditions in which cells may assume adipocyte characteristics, including foam cells of atherosclerotic plaques (Fredrickson, et al., The Metabolic Basis of Inherited Disease (Stanbury, et al. (eds.), 4th Ed., pp. 604–655, McGraw Hill Book Co., Inc., New York (1978)); Minor, et al., *J. Lipid Res.* 30:189–197 (1989)) and, in a number of rare conditions, such as ichthyosis (Chanarin, et al., *Brit. Med. J.* 1:553–555 (1975); Williams, et al.,*J. Inher. Metab. Dis.* 11:131–143 (1988)), in which a variety of cells become lipid-laden. One approach to understanding adipocyte function has centered on examining the fibroblastic cell lines that may be stimulated to differentiate into adipocytes in culture (Green, et al., *Cell* 1:113–116 (1974); Green, et al., *Cell* 5:19–27 (1975)), with special emphasis on describing proteins unique to adipocytes (see, e.g., Spiegleman, *Trends Genet.* 4:203–207 (1988) and Ringold, et al., *Recent Prog. Horm. Res.* 44, 115–140 (1988) for a review). Interest in such proteins is heightened by the evidence that fat cell size, which is directly related to lipid content, is determined by a "set point" possibly regulated by signals emanating from the adipose cell (Faust, et al., *Science* 197:393–396 (1977)).

The intracellular lipid droplet of adipocytes, the locus of stored food energy, has at its periphery a complex structure which alters with the developmental and physiological state of the cell. Electron microscopic studies have shown that the lipid droplets from both native and cultured cells are surrounded by a well developed network of filaments (Wood, *Anat. Rec.* 157:437–448 (1967); Novikoff, et al.,*J. Cell Biol.* 87:180–196 (1980); and Franke, et al., *Cell* 49:131–141 (1987)) as well as endoplasmic reticulum cisternae and tubules (Slavin, *Anat. Rec.* 195:63072 (1979); Cushman, S. W., *J. Cell Biol.* 46:326–341 (1970); Blanchette-Mackie, et al., *Int. J. Obesity* 8:67–73 (1984)), which may extend into the core of the lipid droplet forming aqueous channels (Blanchette-Mackie, et al., *Int. J. Obesity* 8:67–73 (1984)). In metabolically active adipocytes, the luminal leaflet of the channels contains fatty acid products of triacylglycerol hydrolysis which are visualized under appropriate preparatory procedures as lamellar whorls (Blanchette-Mackie, et al., *Int. J. Obesity,* 8:67–73 (1984)) or lipid domains within the membrane leaflet (Amende, et al., *Cell Tissue Res.* 247:85–89 (1986)). Franke, et al. found by immunofluorescence that the intermediate filament protein, i.e., vimentin, surrounds the lipid droplet, and they found by electron microscopy that regularly spaced intermediate filament-like fibrils are located at the lipid periphery (See, *Cell* 49:131–141 (1987)). It was concluded that the lipid droplet is encaged in a vimentin-containing structure.

For several years, hormonal control of metabolic processes and protein phosphorylation in isolated adipocytes have been investigated. Recently, a prominent phosphoprotein in whole cell extracts was identified that is a substrate for cAMP-protein kinase (i.e., A-kinase) (Egan, et al., *J. Biol. Chem.* 265:18769–18775 (1990)). Using this phosphoprotein as a model A-kinase substrate, evidence was presented that in the intact cell, insulin stimulates the dephosphorylation of the protein by a mechanism independent of insulin's ability to lower cAMP, i.e., insulin activates a phosphatase that removes those phosphates inserted by A-kinase.

As of yet, however, the metabolic processes by which metabolites traffic in and out of the lipid droplet still remain a mystery. Moreover, very little is known about the biochemical composition of the surface of such lipid droplets. In order to truly understand the biochemical make-up of the surface of the lipid droplet and the role it plays in allowing metabolites to traffic in and out of the lipid droplet, there exits a need for specific knowledge of the proteins or other molecules on the surface that may be involved in lipid metabolism and trafficking. As previously mentioned, abnormal lipid depositions have been identified in a number of pathophysiological conditions in which cells assume adipocyte characteristics, (e.g., foam cells of atherosclerotic plaques) and, in a number of rare conditions (e.g., ichthyosis) in which a variety of cells become lipid-laden. As such, there exits a need for a definitive marker which can differentiate true adipocytes from non-adipocyte cells which, as a result of pathophysiological conditions, assume adipocyte characteristics and become lipid-laden. The present invention remedies these needs.

SUMMARY OF THE INVENTION

In one aspect, the present invention provides isolated nucleic acid sequences, i.e., polynucleotides, which encode a family of perilipin proteins. More particularly, the present invention provides a DNA sequence which is transcribed into an mRNA of about 3.4 kb which encodes a human perilipin protein, the perilipin protein expressed in human adipocytes and having an amino acid sequence comprising Sequence I.D. No. 6. Moreover, the present invention provides an isolated DNA sequence encoding a perilipin protein having an amino acid sequence selected from the group consisting of Sequence I.D. No. 2 and Sequence I.D. No. 4.

In another aspect, the present invention provides isolated, substantially purified perilipin proteins which are useful as markers for differentiating true adipocytes from non-adipocyte cells which, as a result of pathophysiological conditions, assume adipocyte characteristics and become lipid-laden. More particularly, the present invention provides an isolated, substantially purified human perilipin protein encoded by an mRNA of about 3.4 kb, the perilipin protein expressed in human adipocytes and having an amino acid sequence comprising Sequence I.D. No. 6. Additionally, the present invention provides an isolated, substantially purified perilipin protein having an amino acid sequence selected from the group consisting of Sequence I.D. No. 2 and Sequence I.D. No. 4. Moreover, the present invention provides a murine perilipin protein encoded by an mRNA of about 1.5 kb, the perilipin protein capable of binding to an antibody which binds to the amino-terminus of rat perilipin and wherein the mRNA is capable of hybridizing to Sequence I.D. No. 1 under appropriate hybridization conditions.

In yet another aspect, the present invention provides a recombinant DNA molecule comprising an isolated DNA sequence contained in a recombinant vector (e.g., a plasmid or viral vector), the DNA sequence encoding a perilipin protein. In a preferred embodiment, the encoding segment is present in an expression vector operably linked to an expression control sequence. Additionally, the present invention relates to a cell containing the recombinant DNA molecule. Suitable host cells include procaryotes (such as bacteria, including E. coli) and both lower eucaryotes (for example yeast) and higher eucaryotes (for example, mammalian cells). Introduction of the recombinant molecule into the host cell can be effected using methods known in the art. Moreover, the present invention provides a method for producing a substantially pure perilipin protein, the method comprising: (a) growing a culture of cells comprising an expression vector containing an isolated DNA sequence operably linked to a an expression control sequence, the isolated DNA sequence encoding a perilipin protein; and (b) expressing the perilipin protein from the expression vector and recovering the protein therefrom.

In a further aspect, the present invention provides a method for detecting the presence of a polynucleotide sequence encoding a perilipin protein in a biological sample, the method comprising: (a) contacting the sample, under hybridization conditions, with a nucleic acid probe capable of selectively hybridizing to the polynucleotide sequence to form a hybridization complex; (b) detecting the formation of the hybridization complex as an indication of the presence of the polynucleotide sequence in the sample. In this method, the nucleic acid probe consists of a sequence from Sequence I.D. No. 1, Sequence I.D. No. 3 or Sequence I.D. No. 5. Preferably, this method further comprises, before step (a), the step of amplifying a subsequence of a perilipin gene by the polymerase chain reaction (PCR).

In yet a further aspect, the present invention provides a method for detecting the presence of a perilipin protein in a biological sample, the method comprising: (a) contacting the biological sample with a substantially purified immunoglobulin that specifically binds a perilipin protein; (b) allowing the immunoglobulin to bind to the perilipin protein; (c) removing the immunoglobulin which does not bind to the perilipin protein; and (d) detecting the presence of the bound immunoglobulin. As such, the present invention provides an immunoglobulin which specifically binds to a perilipin protein having an amino acid sequence selected from the group consisting of Sequence I.D. No. 2 and Sequence I.D. No. 4. The present invention also provides an immunoglobulin which specifically binds to a perilipin protein encoded by an mRNA of about 3.4 kb and having an amino acid sequence comprising Sequence I.D. No. 6.

Other advantages, objects, features and embodiments of the present invention will become apparent from the description which follows.

BRIEF DESCRIPTION OF THE DRAWINGS

FIGS. 2A & B. Localization of proteins and phosphoproteins in gross fractions of adipocyte homogenates. Isolated adipose cells were loaded with $^{32}$P and homogenized. The homogenate fractions resulting from centrifugation at 38,000×g for 30 min are: S, supernate; M, membranes; and F, fat cake. Control cells were maintained in 10 nM PIA, and stimulated cells were incubated with 1 $\mu$M isoproterenol, 0.5 unit/ml adenosine deaminase to metabolize both endogenous and exogenous adenosine, and 1 $\mu$M cyclopentylxanthine, an adenosine receptor antagonist. An equivalent portion of each fraction, representing approximately 3% of the material derived from the epididymal adipocytes of one 200-g rat, were processed through SDS-Page. A, silver stain; B, autoradiogram. Arrow is at 62-kDa.

FIGS. 3A–C. Comparison of proteins and phosphoproteins in extracted lipid samples from control and stimulated adipocytes. Isolated adipose cells were loaded with $^{32}$P, fractionated, and the fat cakes extracted. The cell incubation conditions were as described in FIG. 2. A, silver stain; B, Coomassie stain; C, autoradiogram.

A. The structure of the 3.0 kb mRNA for perilipin A is diagramed. The open box represents sequences that are common to perilipin A and B. The striped box indicates the downstream region of A. The predicted structure of the 3.9 kb mRNA B is also diagramed. The open boxes and striped boxes are sequences that are shared with perilipin A. The black box contains the B sequences that are removed during processing to generate the 3.0 kb mRNA. Lines indicate relative positions of the common, A and B probes. Orientation and position of the oligonucleotides used for RT-PCR are indicated. Oligo 1 lies within the A sequences downstream of the presumptive 3'-splice junction. Oligo 2 lies within the B sequences downstream of the 5'-splice junction.

B. Lane 2 is the DNA product derived from the RT-PCR reaction of rat adipocyte RNA (See, FIG. 9A) and analyzed by agarose gel electrophoresis. Lane 1 is molecular weight marker φX-RF DNA digested with Hae III restriction enzyme. Identical DNA blots were hybridized with common, B and A probes, as indicated.

Figure 10:
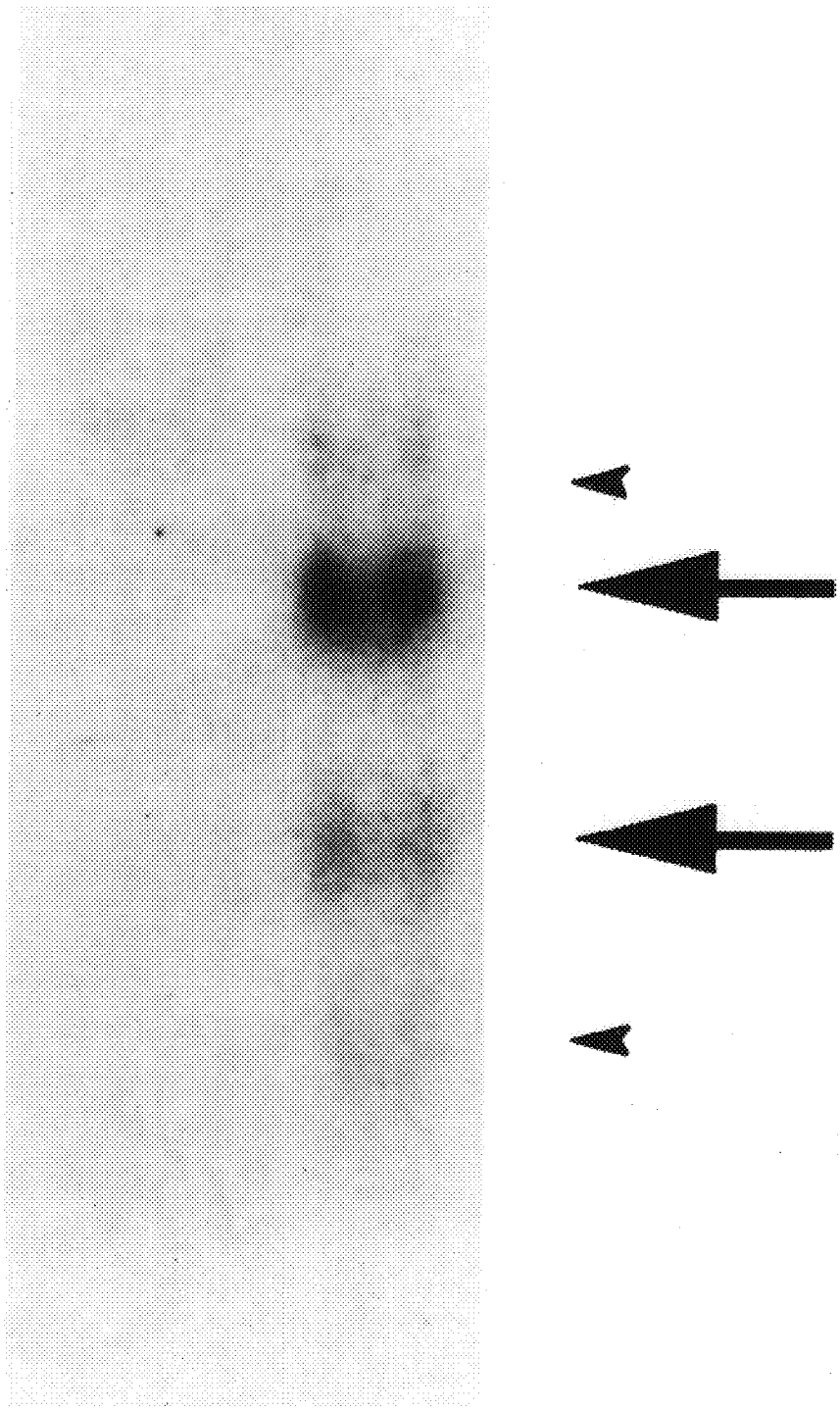

FIG. 10. Expression of perilipin RNA during adipocyte differentiation. Total RNA was isolated from 3T3-L1 confluent (0 day) pre-adipocytes and differentiated (10 day) adipocytes and analyzed by RNA blot hybridization to the common perilipin probe (See, FIG. 7). Arrows indicate positions of the two major and two minor hybridizing RNAs.

Figure 11:
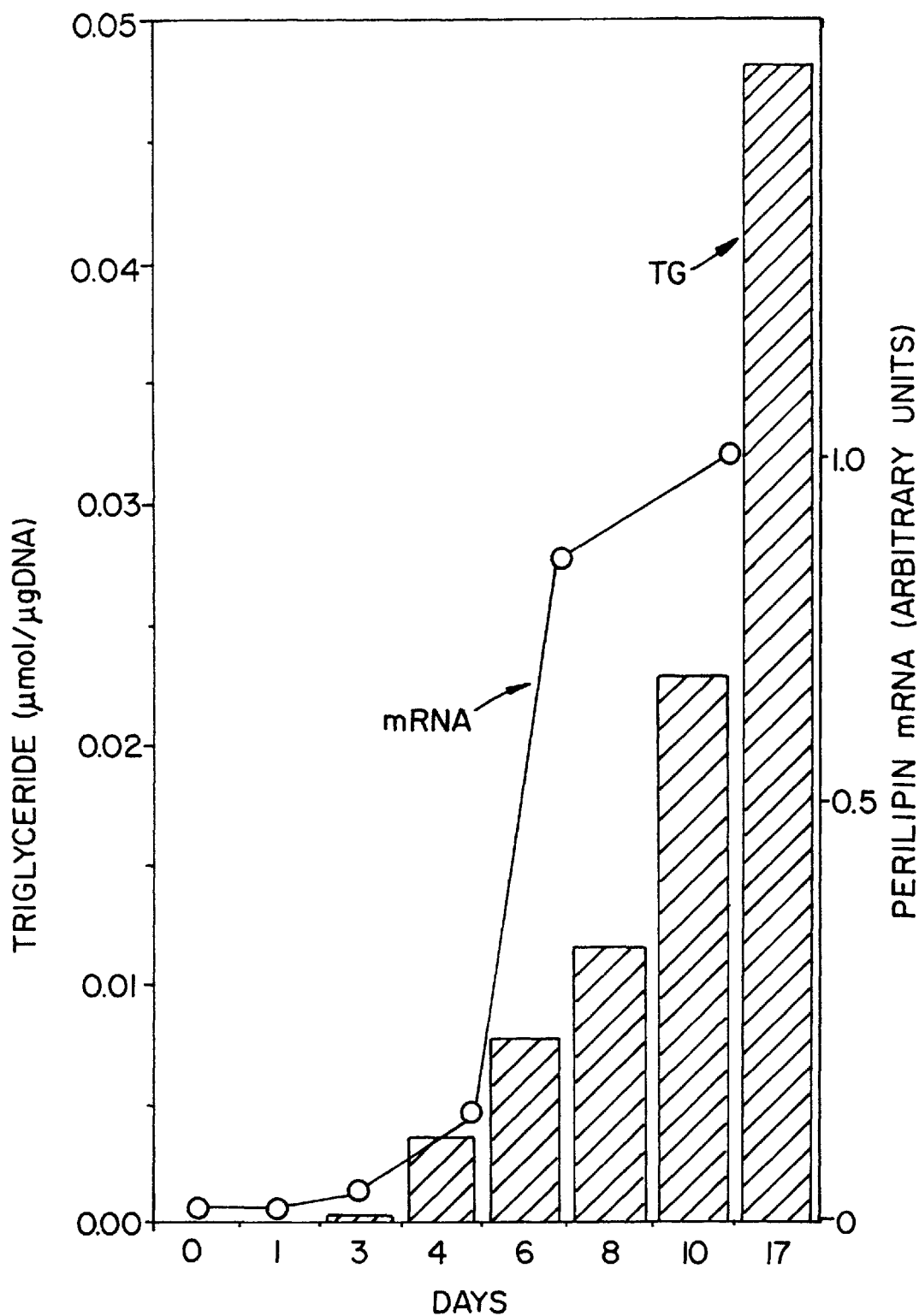

FIG. 11. Triacylglycerol accumulation and perilipin expression in differentiating 3T3-L1 cells. 3T3 cells were stimulated to differentiate into adipocytes according to Rubin, et al. (*J. Biol. Chem.* 253:7570 (1978)) by addition of dexamethasone at Day 0. The hatched bars show triglyceride accumulation at the indicated times, and the open circles show perilipin mRNA accumulation. Sampling time of cells is as indicated on the horizontal axis, with the exception of the three most rightward open circles, which represent samples taken at days 5, 7, and 14 days. Perilipin mRNA was quantitated by densitometric scanning of Northern blots and is expressed in arbitrary units.

Definitions

Nucleic Acids

"Nucleic acid," as used herein, refers to a deoxyribonucleotide (DNA) or ribonucleotide (RNA) in either single- or double-stranded form, and unless otherwise limited, encompasses known analogs of natural nucleotides which can function in a manner similar to the naturally occurring nucleotides.

The phrase "nucleic acid sequence" refers to a single- or double-stranded polymer of deoxyribonucleotide or ribonucleotide bases read from the 5' to the 3' end. It includes both self-replicating plasmids, infectious polymers of DNA or RNA and non-functional DNA or RNA. Additionally, substantial nucleic acid sequence identity exists when a nucleic acid segment will hybridize, under selective hybridization conditions, to a complement of another nucleic acid strand. Nucleotide sizes are given in either kilobases (kb) or base pairs (bp). These are estimates derived from agarose or acrylamide gel electrophoresis.

The phrase "DNA sequence" refers to a single- or double-stranded DNA polymer composed of the nucleotide bases, adenosine, thymidine, cytosine and guanosine.

The phrase "nucleic acid sequence encoding" refers to a nucleic acid sequence which directs the expression of a specific protein or peptide. The nucleic acid sequences include both the DNA sequence that is transcribed into RNA and the RNA sequence that is translated into the protein. The nucleic acid sequence includes both the full length nucleic acid sequence as well as non-full length sequences derived from the full length sequence. It will be understood by those of skill that the sequence includes the degenerate codons of the native sequence or sequences which may be introduced to provide codon preference in a specific host cell.

The term "complementary" refers to a nucleic acid segment that will hybridize, under selective hybridization conditions, to a complement of another nucleic acid strand. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, Kanehisa, *Nucleic Acids Res.* 12:203 (1984), incorporated herein by reference.

"Isolated" or "substantially pure," when referring to nucleic acids, refer to those that have been purified away from other cellular components and contaminants, i.e., other cellular nucleic acids and/or proteins, by standard techniques, including, for example, alkaline/SDS treatment, CsCl banding, column chromatography, and others purification techniques well known in the art. See, e.g., *Methods in Enzymology*, Vol. 152: *Guide to Molecular Cloning Techniques* (Berger and Kimmel (eds.), San Diego: Academic Press, Inc. (1987)), and *Current Protocols in Molecular Biology* (Ausubel, et al., (ed.), Greene Publishing and Wiley-Interscience, New York (1987)), both of which are incorporated herein by reference.

"Nucleic acid probe" refers to an oligonucleotide which binds through complementary base pairing to a subsequence of a target nucleic acid. The nucleic acid probe may be, for example, a DNA fragment prepared by amplification methods such as by PCR or it may be synthesized by either the phosphoramidite method described by Beaucage and Carruthers (*Tetrahedron Lett.* 22:1859–1862 (1981)), or by the triester method according to Matteucci, et al. (*J. Am. Chem. Soc.* 103:3185 (1981)), both of which are incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included as the complementary strand will work equally well in situations where the target is a double stranded nucleic acid.

A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically. It will be understood by those of skill that minor mismatches can be accommodated by reducing the stringency of the hybridization media. For discussions of nucleic acid probe design and annealing conditions, see, e.g., Sambrook, et al., *Molecular Cloning: A Laboratory Manual* (2nd Ed., Vols. 1–3, Cold Spring Harbor Laboratory (1989)), *Methods in Enzymology*, Vol. 152, *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987)), all of which are incorporated herein by reference.

The phrases "expression control sequence" or "expression control cassette" refer to nucleotide sequences which are capable of affecting expression of a structural gene in a host compatible with such sequences. Such cassettes include at least a promoter and, optionally, transcription termination signals. The term "promoter" refers to a region of DNA upstream from the structural gene and involved in the recognition and binding of a DNA polymerase and other proteins necessary to initiate transcription. Additional factors necessary or helpful in effecting expression may also be used as described herein.

The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Techniques for nucleic acid manipulation, such as subcloning nucleic acid sequences encoding polypeptides into expression vectors, labelling probes, DNA hybridization, and so on are described generally, for example, in Sambrook, et al. (1989) supra., Berger and Kimmel, (1987), supra. or Ausubel, et al., (1987), supra., both of which are incorporated herein by reference.

"Expression vectors," "cloning vectors" or "vectors" are often plasmids or other nucleic acid molecules that are able to replicate in a chosen host cell. Expression vectors may replicate autonomously, or they may replicate by being inserted into the genome of the host cell using methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction and in a mammalian cell for expression.

The term "plasmid" refers to an autonomous self-replicating circular DNA molecule and includes both the expression and nonexpression types. Where a recombinant microorganism or cell culture is described as hosting an "expression plasmid," this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "selectively hybridizing to" refers to a nucleic acid that hybridizes duplexes or binds only to DNA sequences encoding one protein or portions thereof when the DNA sequences encoding the protein are present in a cDNA library. A DNA sequence which selectively hybridizes to a given target sequence can include sequences which are shorter or longer than the target sequence so long as they meet the functional test set forth. Hybridization conditions are specified herein along with the source of the cDNA library. Typically, the hybridization is done in a Southern blot protocol using a 0.2×SSC, 0.1% SDS, 65° C. wash.

The term "SSC" refers to a citrate-saline solution of 0.15 M sodium chloride and 15 mM sodium citrate (pH 7.0). Solutions are often expressed as multiples or fractions of this concentration. For example, 6×SSC refers to a solution having a sodium chloride and sodium citrate concentration of 6 times this amount or 0.9 M sodium chloride and 90 mM sodium citrate. 0.2×SSC refers to a solution 0.2 times the SSC concentration or 0.03 M sodium chloride and 3 mM sodium citrate.

Proteins

The terms "peptide", "polypeptide" or "protein" are used interchangeably herein. The term "substantial identity," when referring to polypeptides, indicates that the polypeptide or protein in question is at least about 70% identical to an entire naturally occurring protein (native) or a portion thereof, and preferably at least about 95% identical.

As used herein, the terms "isolated," "substantially pure" and "biologically pure" are used interchangeably and describe a protein that has been separated from components which naturally accompany it. Typically, a monomeric protein is substantially pure when at least about 60% to about 75% of a sample exhibits a single polypeptide backbone. Minor variants or chemical modifications typically share the same polypeptide sequence. A substantially purified protein will typically comprise about 85% to about 90% of a protein sample, more usually about 95% and, more preferably, it will be over about 99% pure. Protein purity or homogeneity may be indicated by a number of means well known in the art, such as, for example, by polyacrylamide gel electrophoresis (PAGE) of a protein sample, followed by visualizing a single polypeptide band on a polyacrylamide gel upon staining. For certain purposes, high resolution will be needed and, thus, HPLC or other similar means can be utilized for purification in such instances.

A polypeptide is substantially free of naturally-associated components when it is separated from the native contaminants which accompany it in its natural state. Thus, a polypeptide which is chemically synthesized or synthesized in a cellular system different from the cell from which it naturally originates will be substantially free from its naturally-associated components.

The proteins of the present invention can be purified to substantial homogeneity by standard techniques well known in the art, including, for example, selective precipitation with such substances as ammonium sulfate, column chromatography, immunopurification methods, and other purification techniques. See, e.g., Scopes, *Protein Purification: Principles and Practice* (Springer-Verlag: New York (1982)), incorporated herein by reference.

Immunoglobulins

As used herein, "immunoglobulin" refers to molecules which have specific immunoreactive activity. Antibodies are typically tetramers of immunoglobulin molecules. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains, Heavy chain types are alpha, gamma, delta, epsilon and mu. The carboxy terminal portions of immunoglobulin heavy and light chains are constant regions, while the amino terminal portions are encoded by the myriad of immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (See, e.g., Huston, et al., *Proc. Nat. Acad. Sci. U.S.A.*, 85:5879–5883 (1988) and Bird, et al., *Science* 242:423–426 (1988), which are incorporated herein by reference). (See generally, Hood, et al., *"Immunology,"* (Benjamin, N.Y., 2nd ed. (1984)), and Hunkapiller and Hood, *Nature* 323:15–16 (1986), which are incorporated herein by reference). Single-chain antibodies, in which genes for a heavy chain and a light chain are combined into a single coding sequence, may also be used.

"Monoclonal antibodies" may be obtained by various techniques familiar to those skilled in the art. Briefly, spleen cells from an animal immunized with a desired antigen are immortalized, commonly by fusion with a myeloma cell. (See, e.g., Kohler and Milstein, *Eur. J. Immunol.* 6:511–519 (1976), incorporated herein by reference). Alternative methods of immortalization include, for example, transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques including, for example, injection into the peritoneal cavity of a vertebrate host.

DETAILED DESCRIPTION OF THE INVENTION

The present invention provides isolated nucleic acid sequences, i.e., polynucleotides, which encode a family of perilipin proteins. The present invention also provides isolated, substantially purified perilipin proteins which are useful as markers for differentiating true adipocytes from non-adipocyte cells which, as a result of pathophysiological conditions, assume adipocyte characteristics and become lipid-laden. The present invention further provides methods for producing a substantially purified perilipin protein and methods for detecting the presence of such proteins in biological samples.

Perilipin was first identified in rat adipocytes. It has been discovered that perilipin, found at the surface of the lipid storage droplets, is the major cAMP-dependent protein kinase (i.e., A-kinase) substrate in adipocytes. Using antiperilipin serum, two related classes of cDNAs have been isolated from a lambda gt11 rat adipocyte cDNA expression library. The predicted 56,870 Da product of perilipin A cDNA (i.e., Sequence I.D. No. 1) includes seven peptide sequences obtained from proteolytic digestion of the purified ~62-kDa perilipin, a protein which is present in unstimulated adipocytes. Moreover, the predicted 56,870 Da product of perilipin A cDNA contains six consensus A-kinase phosphorylation sites, consistent with the number of phosphates added to perilipin upon activation of A-kinase in the cell. These data indicate that perilipin A corresponds to the ~62-kDa phosphoprotein identified in unstimulated adipocytes.

The second cDNA class, corresponding to Sequence I.D. No. 3, is predicted to encode a 46,420 Da variant protein, perilipin B, which is identical to perilipin A in its N-terminal 406 amino acids. Perilipin B lacks three of the six consensus A-kinase sites found in the A form, and is likely to be the ~46-kDa fat-associated, A-kinase substrate identified in adipocyte. Perilipins A and B are both phosphorylated in unstimulated cells and hyperphosphorylated upon elevation of A-kinase activity. The hyperphosphorylation of perilipin A, but not B, causes a dramatic alteration in migration during SDS-PAGE. It appears that the three additional A-kinase sites specific to the carboxyl-terminal region of perilipin A are responsible for this altered behavior during SDS-PAGE. Since immunoblot analysis of subcellular fractions indicate that both perilipin A and B fractionate exclusively with lipid, and since immunofluorescence studies detect reactive epitopes only in tight association with the lipid droplet, it appears that perilipin B, like perilipin A, is localized at the periphery of the droplet.

It has been determined that perilipin A is encoded by an mRNA of about 3.0 kb, whereas perilipin B is encoded by an mRNA of about 3.9 kb. Molecular studies indicate that the 3.0 kb and 3.9 kb mRNA species, for perilipins A and B, respectively, derive from alternative splicing of a common precursor. Further, analyses of genomic sequences indicate that the perilipins are encoded by a single-copy gene. Taken together, these data suggest that the differences in structure between the two mRNA forms derive from an additional, internal sequence specific to the 3.9 kb mRNA (See, FIG. 9A). The two mRNAs may use identical transcription initiation and polyadenylylation sites. The considerably greater abundance of perilipin A mRNA relative to that for perilipin B is consistent with the relative levels of A and B proteins as monitored by immunoblotting and phosphate incorporation.

Moreover, Northern analysis of mRNA extracted from murine adipocytes reveals that these adipocytes also contain multiple perilipin proteins. RNA was extracted from murine adipocytes by the RNAzol B (Cinna/Biotecx Laboratories International, Inc., Friendswood, Tex.) and Northern analysis performed according to Wahl, et al. (*Meth. Enzymol.* 152:572–581)). The blots were probed with full length rat perilipin A cDNA. The following four mRNA bands were observed: ~3.9 kb, ~3.0 kb, ~1.8 kb and ~1.5 kb. In the murine adipocytes, both cultured and primaly, the relative abundance of the message form is: 3.0>1.8≧3.9>1.5. The most abundant message, i.e., 3.0 kb, encodes perilipin A (~62-kDa), whereas the 3.9 kb message encodes perilipin B (~46-kDa). The translation product of the 1.8 kb message is expected to be a protein found at ~47 kDa which is slightly larger than perilipin B. The translation product of the 1.5 kb message has yet to be identified, but a similar 1.5 kb message along with its translation product have been found in murine adrenal cortical cells (See, Example V, infra.).

The discovery of multiple perilipin proteins in rat and murine adipocytes has spurred an investigation into whether or not perilipin is present in human adipocyte cells. As such, a human adipocyte cDNA library was obtained from Clontech (Palo Alto, Calif.) and positive closes were identified using a full length cDNA probe based on rat perilipin A (See, Sequence I.D. No. 1). In cloning the human perilipin protein, it has been discovered that the DNA is transcribed into an mRNA of about 3.4 kb which, in turn, encodes a human perilipin protein having an amino acid sequence comprising Sequence I.D. No. 6. It has further been determined that amino acids 14 to 421 of the human perilipin protein are 85% identical (95% similar) to amino acids 9 to 419 of perilipin A. It is expected that since the amino acid sequences for perilipin A and B diverge after amino acid 406, the human perilipin protein of Sequence I.D. No. 6 is a homolog of perilipin A. As with both rat perilipin A and B, the human perilipin protein is expressed in adipocytes. Moreover, as with the rodent adipocytes, it has been determined by Western blot analysis that two proteins of approximately equal abundance are found in human adipocytes, one of approximately 65-kDa and the other of approximately 60-kDa. It is interesting to note that this pattern differs from rodent adipocytes which have a major form at 62-kDa (i.e., perilipin A) and, two minor forms, one at 46-kDa (i.e., perilipin B) and one at 47-kDa (as yet unnamed)

RNA blot hybridization for various rat tissues reveals that perilipin proteins are primarily expressed in adipocytes. This data, however, does not exclude a low level expression of perilipin in non-adipose tissue which accumulate few, small lipid droplets, but if perilipin mRNA is present in these non-adipose tissues, it does not represent more than 0.002% of total tissue mRNA. Perilipin has, in fact, been found in adrenal cortical cells, but at an abundance equal to about 2 to 5 percent of that found in adipocytes; this is true for both mRNA abundance and protein abundance. Immunoaffinity purified antibodies prepared against full length rat perilipin A (i.e., Sequence I.D. No. 1) recognize two major and two minor protein bands in Western blots of whole adrenal cortical cell lysates. One major band that migrates as a ~62-kDa protein is perilipin A which, as expected, exhibits altered migration in SDS-PAGE (to ~65-kDa) when obtained from cells that had been stimulated with either ACTH or forskolin, both of which elevate cAMP in these cells. The second major band migrates as a protein of ~42-kDa and is equal in intensity in the Western blot to perilipin A. This smaller species is not apparent above the background staining in Western blots of adipocytes. This new protein is identified as perilipin C. Finally, one of the two minor bands seen in the adrenal Western blots corresponds to the ~46-kDa perilipin B of adipocytes, and the second minor band migrates slightly above perilipin B (~47-kDa). Thus, it has been found that the adrenal cortical cells contain a major form of perilipin (~42-kDa) and a minor form of perilipin (~47-kDa) which are either present in relatively low abundance or absent from rat adipocytes.

Although perilipin has been found in adrenal cortical cells, it has been discovered that perilipin can be used as a marker for differentiating true adipocytes from non-adipocyte cells. Abnormal lipid depositions have been identified in a number of pathophysiological conditions in which cells assume adipocyte characteristics, (e.g., foam cells of atherosclerotic plaques) and, in a number of rare conditions (e.g., ichthyosis) in which a variety of cells become lipid-laden. As such, there exits a need for a definitive marker which can differentiate true adipocytes from non-adipocyte cells which, as a result of pathophysiological conditions, assume adipocyte characteristics and become lipid-laden. Perilipin has been found to be such a marker and, thus, it can be used to unequivocally differentiate true adipocytes from non-adipocyte cells.

Moreover, the tissue specificity and developmental expression pattern of the perilipin proteins, their location at the surface of the lipid droplet, and their phosphorylation by A-kinase concomitant with activation of lipolytic activity suggest a role for these proteins in lipid metabolism. Recently, it has been demonstrated that hormone sensitive lipase, the rate-limiting enzyme of lipolysis, translocates to the lipid droplet surface upon lipolytic activation of adipocytes (Egan, et al., *Proc. Natl. Acad. Sci.* 89:8537–8541 (1992)). As such, one potential role for perilipin may be as a barrier to deny access of the lipase to the lipid of unstimulated cells, whereas, upon phosphorylation of perilipin by A-kinase, the lipid surface may become exposed. Alternatively, perilipin may serve as a "docking" protein for the lipase during stimulated conditions or may be required to establish or maintain the organization of the lipid droplet.

The perilipin proteins exhibit sequence similarity with only a single additional protein (or gene) listed in the current data bases (Jang, et al., *Proc. Natl. Acad. Sci.* 89:7856–7860 (1992)). The highly significant, albeit limited, relationship (~65% similarity through 105 amino acids), between the perilipins and ADRP is intriguing, especially since they share a common tissue specificity. In contrast to the perilipins, which associate exclusively with the lipid droplet surface, ADRP is associated with a particulate fraction in or near the plasma membrane. It is, nevertheless, probable that the perilipins and ADRP are involved in related adipocyte processes. It may be that the perilipins and ADRP interact with a common factor involved in lipid metabolism that shuttles to and from the lipid droplet.

Using the methodology set forth herein, one of skill can produce perilipin proteins. In general, the DNA encoding the perilipin proteins are first cloned or isolated in a form suitable for ligation into an expression vector. After ligation, the vectors containing the DNA fragments or inserts are introduced into a suitable host cell for expression of the recombinant perilipin polypeptides. The polypeptides are then isolated from the host cells.

A. General Recombinant DNA Methods

This invention relies on the use of conventional techniques and procedures in the field of recombinant genetics. Two text books which describe in great detail the general methods of use in this invention are Sambrook, et al., *Molecular Cloning, A Laboratory Manual* (Cold Spring Harbor Publish., Cold Spring Harbor, N.Y. 2nd ed. (1989)), *Methods in Enzymology*, Vol. 152: *Guide to Molecular Cloning Techniques* (Berger and Kimmel (eds.), San Diego: Academic Press, Inc. (1987)) and Kriegler, *Gene Transfer and Expression: A Laboratory Manual* (W. H. Freeman, N.Y. (1990)), all of which are incorporated herein by reference.

B. Cloning Methods for the Isolation of Nucleic Acid Sequences Encoding The Perilipin Proteins The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the perilipin proteins of the invention, such as subcloning nucleic acid sequences encoding polypeptides into expression vectors, labelling probes, DNA hybridization, and the like are described generally in Sambrook, et al., supra., and Berger and Kimmel, (1987), supra., both of which are incorporated herein by reference.

Recombinant DNA techniques can be used to produce the perilipin polypeptides. In general, the DNA encoding the perilipin proteins are first cloned or isolated in a form suitable for ligation into an expression vector. After ligation, the vectors containing the DNA fragments or inserts are introduced into a suitable host cell for expression of the recombinant perilipin polypeptides. The polypeptides are then isolated from the host cells.

In general, the nucleic acid sequences of the genes encoding the perilipin proteins are cloned from DNA sequence libraries that are made to encode copy DNA (i.e., cDNA) or genomic DNA. The particular sequences can be located by hybridizing with an oligonucleotide probe, the sequences of which can be derived from Sequence I.D. Nos.: 1, 3 and 5. The desired target sequences may also be obtained using polymerase chain reaction (PCR) primers which amplify either the entire gene, cDNA or portions there of. PCR primers can be selected from the sequences provided herein. Alternatively, where the sequence is cloned into an expression library, the expressed recombinant the perilipin can be detected immunologically with antisera or purified antibodies made against the perilipin.

To make the cDNA library, one should choose a source that is rich in mRNA (e.g., adipocytes). The mRNA can then be made into cDNA, ligated into a recombinant vector, and transfected into a recombinant host for propagation, screening and cloning. Methods for making and screening cDNA libraries are well known. See, Gubler and Hoffman, (*Gene* 25:263–269 (1983)), Sambrook, et al., supra., and Berger and Kimmel, (1987), supra.

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al., supra., and Berger and Kimmel, (1987), supra. Recombinant phage are analyzed by plaque hybridization as described in Benton and Davis (*Science*, 196:180–182 (1977)). Colony hybridization is carried out as generally described in Grunstein, et al. (*Proc. Natl. Acad. Sci. USA.* 72:3961–3965 (1975)).

An alternative method combines the use of synthetic oligonucleotide primers with polymerase extension on an mRNA or DNA template. This polymerase chain reaction (PCR) method amplifies nucleic acid sequences of the perilipin genes directly from mRNA, from cDNA, from genomic libraries or cDNA libraries. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of perilipin mRNA in physiological samples, for nucleic acid sequencing, or for other purposes. U.S. Pat. Nos. 4,683,195 and 4,683,202 describe this method. Genes amplified by the PCR reaction can be purified from agarose gels and cloned into an appropriate vector.

Appropriate primers and probes for amplifying and identifying perilipin proteins are generated from comparisons of the sequences provided herein. In brief, oligonucleotide primers are complementary to the borders of the DNA region to be amplified are synthesized. The polymerase chain reaction is then carried out using the two primers. For a general overview of PCR, see, e.g., *PCR Protocols: A Guide to Methods and Applications* (Innis, Gelfand, Sninsky and White, eds.), Academic Press, San Diego (1990), incorporated herein by reference.

Oligonucleotides that are useful as probes can be chemically synthesized according to the solid phase phosphoramidite triester method first described by Beaucage and Caruthers (*Tetrahedron Letts.* 22(20):1859–1862 (1981)) using an automated synthesizer, as described in Van Devanter, et al. (*Nucleic Acids Res.* 12:6159–6168 (1984)). Purification of oligonucleotides is by either native acrylamide gel electrophoresis or by anion-exchange HPLC as described by Pearson and Reanier (*J. Chrom.* 255:137–149 (1983)).

The sequences of the cloned genes and synthetic oligonucleotides can be verified using the chemical degradation method of Maxam and Gilbert (*Methods in Enzymology* 65:499–560 (1980)). The sequence can be confimed after the assembly of the oligonucleotide fragments into the double-stranded DNA sequence using the method of Maxam and Gilbert, supra., or the chain termination method for sequencing double-stranded templates of Wallace, et al. (*Gene* 16:21–26 (1981)). Southern Blot hybridization techniques are carried out according to Southern, et al. (*J. Mol. Biol.*, 98:503 (1975)).

Synthetic oligonucleotides can also be used to construct genes. This is done using a series of overlapping oligonucleotides usually 40–120 bp in length, representing both the sense and nonsense strands of the gene. These DNA fragments are then annealed, ligated and cloned.

Moreover, the genes, i.e., polynucleotides, encoding the perilipin proteins can be cloned using intermediate vectors before transformation into mammalian cells for expression. These intermediate vectors are typically prokaryote vectors or shuttle vectors. The perilipin proteins can be expressed in either prokaryotes or eukaryotes.

In summary, the perilipin genes can prepared by probing or amplifying select regions of a mixed cDNA or genomic pool using the probes and primers generated from the sequences provided herein.

C. Expression of Perilipin Polypeptides

Once the polynucleotides encoding the perilipin proteins are isolated and cloned, one may express the desired polypeptides in a recombinantly engineered cell such as bacteria, yeast, insect (especially employing baculoviral vectors), and mammalian cells. It is expected that those of skill in the art are knowledgeable in the numerous expression systems available for expression of the DNA encoding the perilipin proteins. No attempt to describe in detail the various methods known for the expression of proteins in prokaryotes or eukaryotes will be made.

In brief summary, the expression of natural or synthetic nucleic acids encoding perilipin polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the perilipin proteins. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coil* tryptophan biosynthetic pathway as described by Yanofsky, *Bacteriol.* 158:1018–1024 (1984), and the leftward promoter of phage lambda ($P_L$) as described by Herskowitz and Hagen, *Ann. Rev. Genet.*, 14:399–445 (1980). The inclusion of selection markers in DNA vectors transformed in *E. coli* is also useful. Examples of such markers include genes specifying resistance to ampicillin, tetracycline, or chloramphenicol. See, Sambrook, et al. for details concerning selection markers for use in *E. coli.*

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the perilipin proteins are available using *E. coil,* Bacillus sp. and Salmonella (Palva, et al., *Gene* 22:229–235 (1983); Mosbach, et al., *Nature* 302:543–545 (1983). *E. coli* systems are presently preferred.

The perilipin polypeptides produced by prokaryote cells may not necessarily fold properly. During purification from *E. coli,* the expressed polypeptides may first be denatured and then renatured. This can be accomplished by solubilizing the bacterially produced proteins in a chaotropic agent such as guanidine HCI and reducing all the cysteine residues with a reducing agent such as beta-mercaptoethanol. The polypeptides are then renatured, either by slow dialysis or by gel filtration. U.S. Pat. No. 4,511,503.

When expressing the perilipin proteins in *S. typhimurium,* one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium,* the foreign gene is incorporated into the chromosome by homologous recombination between the flanking sequences and chromosomal DNA.

An example of how this can be achieved is based on the his operon of Salmonella. Two steps are involved in this process. First, a segment of the his operon must be deleted in the Salmonella strain selected as the carrier. Second, a plasmid carrying the deleted his region downstream of the gene encoding the perilipin proteins is transformed into the his Salmonella strain. Integration of both the his sequences and a gene encoding a perilipin protein occurs, resulting in recombinant strains which can be selected as his$^+$.

Detection of the expressed protein is achieved by methods known in the art and include, for example, radioimmunoassays, Western blotting techniques or immunoprecipitation. Purification from *E. coli* can be achieved following procedures described in U.S. Pat. No. 4,511,503.

D. Expression in Eukaryotes

Standard eukaryotic transfection methods are used to produce mammalian, yeast or insect cell lines which express large quantities of the peritipin proteins which are then purified using standard techniques. See, e.g., Colley, et al., *J. Biol. Chem.* 264:17619–17622 (1989), and "Guide to Protein Purification," in Vol. 182 of *Methods in Enzymology* (Deutscher (ed.), 1990), both of which are incorporated herein by reference.

Transformations of eukaryotic cells are performed according to standard techniques as described by Morrison, *J. Bact.* 132:349–351 (1977), or by Clark-Curtiss and Curtiss, *Methods in Enzymology* 101:347–362 (Wu, et. al., (eds.)), Academic Press, New York (1983).

Any of the well known procedures for introducing foreign nucleotide sequences into host cells can be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (See, Sambrook, et al., supra.). It is only necessary that the particular genetic engineering procedure utilized be capable of successfully introducing at least one gene into the host cell which is capable of expressing a perilipin protein.

The particular eukaryotic expression vector used to transport the genetic information into the cell is not particularly critical. Any of the conventional vectors used for expression in eukaryotic cells can be used. Expression vectors containing regulatory elements from eukaryotic viruses are typically used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors usually comprise selectable markers which result in gene amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with the perilipin encoding sequence under the direction of the polyhedrin promoter or other strong baculovirus promoters.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see, Sambrook, et al., supra., Ch. 16.

The prokaryotic elements that are typically included in the mammalian expression vector include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

The expression vector contains a eukaryotic transcription unit or expression cassette that contains all the elements required for the expression of a perilipin protein DNA in eukaryotic cells. A typical expression cassette contains a promoter operably linked to the DNA sequence encoding a perilipin protein and signals required for efficient polyadenylation of the transcript. The DNA sequence encoding the perilipin protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or *Rous sarcoma* virus and HIV. See, *Enhancers and Eukaryotic Expression* (Cold Spring Harbor Pres, Cold Spring Harbor, N.Y. 1983), which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

After the expression vector is introduced into the cells, the transfected cells are cultured under conditions favoring expression of the perilipin protein which is recovered from the culture using standard techniques 1. Expression in Yeast Synthesis of heterologous proteins in yeast is well known and described. *Methods in Yeast Genetics,* Sherman, et al., Cold Spring Harbor Laboratory (1982) is a well recognized work describing the various methods available to produce a perilipin protein in yeast.

For high level expression of a gene in yeast, it is essential to connect the gene to a strong promoter system and to provide efficient transcription termination/polyadenylation sequences from a yeast gene. Examples of useful promoters include GAL1,10 (Johnson and Davies, *Mol. and Cell. Biol.,* 4:1440–1448 (1984)) ADH2 (Russell, et al., *J. Biol. Chem.,* 258:2674–2682, (1983)), PHO5 (*EMBO J.* 6:675–680, (1982)), and MFα1 (Herskowitz and Oshima, in *The Molecular Biology of the Yeast Saccharomyces,* (Strathern, Jones and Broach, eds.), Cold Spring Harbor Lab., Cold Spring Harbor, N.Y., pp.181–209, (1982)). A multicopy plasmid with a selective marker such as, for example, Leu-2, URA-3, Trp-1, and His-3 is also desirable.

The MFα1 promoter is preferred. The MFα1 promoter, in a host of the α mating-type is constitutive, but is switched off in diploids or cells with the a mating-type. It can, however, be regulated by raising or lowering the temperature in hosts which have a ts mutation at one of the SIR loci. The effect of such a mutation at 35° C. on an a type cell is to turn on the normally silent gene coding for the a mating-type. The expression of the silent a mating-type gene, in turn, turns off the MFα1 promoter. Lowering the temperature of growth to 27° C. reverses the whole process, i.e., turns the a mating-type off and turns the MFα1 on (Herskowitz and Oshima, supra.).

The polyadenylation sequences are provided by the 3'-end sequences of any of the highly expressed genes, like ADH1, MFα1, or TPI (Alber and Kawasaki, *J. Mol. & Appl. Genet.* 1:419–434 (1982).

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., Gene 8:17–24 (1979); Broach, et al, *Gene* 8:121–133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs, *Nature* 275:104–109 (1978); and Hinnen, et al.,*Proc. Natl. Acad. Sci. USA*, 75:1929–1933 (1978). The second procedure does not involve removal of the cell wall. Instead the cells are treated with lithium chloride or acetate and PEG and put on selective plates (Ito, et al., *J. Bact.* 153:163–168 (1983)).

Soluble perilipin proteins can be isolated from yeast by lysing the cells and applying standard protein isolation techniques to the lysates. The monitoring of the purification process can be accomplished by using Western blot techniques or other standard radioimmunoassays.

2. Expression in Insect Cells

The baculovirus expression vector utilizes the highly expressed and regulated *Autographa californica* nuclear polyhedrosis virus (AcMNPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically, and functionally similar to their natural counterparts. In addition, the baculovirus vector utilizes many of the protein modification, processing, and transport systems that occur in higher eukaryotic cells.

Briefly, the DNA sequence encoding a perilipin protein is inserted into a transfer plasmid vector in the proper orientation downstream from the polyhedrin promoter, and flanked on both ends with baculovirus sequences. Cultured insect cell, commonly *Spodoptera frugiperda*, are transfected with a mixture of viral and plasmid DNAs. The virus that develop, some of which are recombinant virus that result from homologous recombination between the two DNAs, are plated at 100–1000 plaques per plate. The plaques containing recombinant virus can be identified visually because of their ability to form occlusion bodies or by DNA hybridization. The recombinant virus is isolated by plaque purification. The resulting recombinant virus, capable of expressing a perilipin protein, is self-propagating in that no helper virus is required for maintenance or replication. After infecting an insect culture with recombinant virus, one can expect to find recombinant protein within 48–72 hours. The infection is essentially lytic within 4–5 days.

There are a variety of transfer vectors into which a perilipin gene can be inserted. For a summary of transfer vectors, see, Luckow and Summers, *Bio/Technology* 6:47–55 (1988). Preferred is the transfer vector pAcUW21 described by Bishop in *Seminars in Virology* 3:253–264 (1992).

3. Expression in Recombinant Vaccinia Virus-infected Cells or Adenovirus-infected Cells In addition to use in recombinant expression systems, the isolated DNA sequences encoding the perilipin proteins can also be used to transform viruses that transfect host cells in the patient. Live attenuated viruses, such as vaccinia or adenovirus, are convenient alternatives for vaccines because they are inexpensive to produce and are easily transported and administered. Vaccinia vectors and methods useful in immunization protocols are described, for example, in U.S. Pat. No. 4,722,848, incorporated herein by reference.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the perilipin polypeptides into plasmids so that they are flanked by viral sequences on both sides. The DNA's encoding the perilipin proteins are then inserted into the virus genome through homologous recombination.

A recombinant adenovirus can be produced, for example, by ligating together two plasmids each containing about 50% of the viral sequence and the DNA sequence encoding a perilipin polypeptide. Recombinant RNA viruses such as the alpha virus can be made via a cDNA intermediate using methods known in the art.

In the case of vaccinia virus (for example, strain WR), the DNA sequence encoding the perilipin proteins can be inserted in the genome by a number of methods including homologous recombination using a transfer vector, pTKgpt-OFIS as described in Kaslow, et al. (*Science* 252:1310–1313 (1991)), which is incorporated herein by reference.

Alternately the DNA encoding the perilipin proteins may be inserted into another plasmid designed for producing recombinant vaccinia, such as pGS62, Langford, C. L., et al., 1986, *Mol. Cell. Biol.* 6:3191–3199. This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding the perilipin polypeptides and by immunodetection techniques using antibodies specific for the expressed perilipin polypeptides. Virus stocks may be prepared by infection of cells such as HELA S3 spinner cells and harvesting of virus progeny.

The recombinant virus of the present invention can be used to induce anti-perilipin antibodies in mammals, such as mice or humans. In addition, the recombinant virus can be used to produce perilipin by infecting host cells in vitro, which in turn express the polypeptide (see section on expression of perilipin in eukaryotic cells, above).

The present invention also relates to host cells infected with the recombinant virus. The host cells of the present invention are preferably mammalian, such as BSC-1 cells. Host cells infected with the recombinant virus express the perilipin proteins on their cell surfaces. In addition, membrane extracts of the infected cells induce protective antibodies when used to inoculate or boost previously inoculated mammals.

4. Expression in Cell Cultures

Perilipin cDNA can be ligated to various expression vectors for use in transforming host cell cultures. The vectors typically contain gene sequences to initiate transcription and translation of the perilipin gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of perilipin protein. Mammalian cell systems often will be in the form of monolayers of cells although mammalian cell suspensions may also be used. Illustrative examples of mammalian cell lines include, for example, VERO and HeLa cells, Chinese hamster ovary (CHO) cell lines, W138, BHK, COS-7 or MDCK cell lines.

As indicated above, the vector, i.e., a plasmid, which is used to transform the host cell, preferably contain s DNA sequences to initiate transcription and sequences to control the translation of the perilipin gene sequence. These sequences are referred to as expression control sequences. Illustrative expression control sequences are obtained from the SV-40 promoter (*Science* 222:524–527 (1983)), the CMV I.E. Promoter (*Proc. Natl. Acad. Sci. USA.* 81:659–663 (1984)) or the metallothionein promoter (*Nature* 296:39–42 (1982)). The cloning vector containing the expression control sequences is cleaved using restriction enzymes and adjusted in size as necessary or desirable and ligated with sequences encoding the perilipin protein by means well known in the art. As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Vrol.* 45:773–781 (1983)).

Additionally, gene sequences to control replication in the host cell may be incorporated into the vector such as those found in bovine papilloma virus type-vectors. See, e.g., Saveria-Campo, "*Bovine Papilloma virus DNA a Eukaryotic Cloning Vector*" in DNA Cloning, Vol. II, A Practical Approach (D. M. Glover, Ed., IRL Press, Arlington, Va., pp. 213–238 (1985)).

The transformed cells are cultured by means well known in the art. For example, as published in *Biochemical Methods in Cell Culture and Virology* (Kuchler, Dowden, Hutchinson and Ross, Inc. (1977)). The expressed perilipin protein is isolated from cells grown as suspensions or as monolayers. The latter are recovered by well known mechanical, chemical or enzymatic means.

G. Purification of the Percihpin Proteins

The perilipin proteins of the present invention can be substantially purified using conventional techniques known to and used by those of skill in the art. In general, the fat cells (i.e., adipocytes) are isolated as set forth in the examples, and lipid is extracted using a solvent such as, for example, acetone. The precipitated perilipin proteins are then solubilized in 8M urea and 1% TRITON® X-100, and the protein mixture is loaded onto a HPLC ion exchange column.

H. Detection of the Perilipin Genes and Perilipin Proteins.

1. Perilipin DNA and RNA Measurement

The present invention also provides methods for detecting the presence or absence of perilipin DNA or RNA in a biological sample. A variety of methods of specific DNA and RNA measurement using nucleic acid hybridization techniques are known to those of skill in the art. See, e.g., Sambrook, et al., supra. and Berger and Kimmel, (1987), supra. For example, one method for evaluating the presence or absence of perilipin DNA in a sample involves a Southern transfer. Briefly, the digested genomic DNA is run on agarose slab gels in buffer and transferred to membranes. Hybridization is carried out using probes as described above. Visualization of the hybridized portions allows the qualitative determination of the presence or absence of perilipin genes.

Similarly, a Northern transfer may be used for the detection of Perilipin mRNA in samples of RNA. In brief, the mRNA is isolated from a given cell sample (e.g., an adipocyte) using an SDS-phenol or acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of a perilipin transcript.

A variety of nucleic acid hybridization formats are known to those skilled in the art. For example, common formats include sandwich assays and competition or displacement assays. Hybridization techniques are generally described in Berger and Kimmel, (1987), supra.; "*Nucleic Acid Hybridization, A Practical Approach*" (Hames, B. D. and Higgins, S. J. (eds.), IRL Press, 1985; Gall and Pardue, (*Proc. Natl. Acad. Sci., U.S.A.* 63:378–383 (1969)); and John, Bumsteil and Jones (*Nature,* 223:582–587 (1969)).

For example, sandwich assays are commercially useful hybridization assays for detecting or isolating nucleic acid sequences. Such assays utilize a "capture" nucleic acid covalently immobilized to a solid support and a labelled "signal" nucleic acid in solution. The clinical sample will provide the target nucleic acid. The "capture" nucleic acid probe and the "signal" nucleic acid probe hybridize with the target nucleic acid to form a "sandwich" hybridization complex. To be effective, the signal nucleic acid cannot hybridize with the capture nucleic acid.

Typically, labelled signal nucleic acids are used to detect hybridization. Complementary nucleic acids or signal nucleic acids may be labelled by any one of several methods typically used to detect the presence of hybridized oligonucleotides. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe oligonucleotides or nucleic acids. Typically, such binding occurs through ligand and anti-ligand interactions as between a ligand-conjugated probe and an anti-ligand conjugated with a signal. The binding of the signal generation complex is also readily amendable to accelerations by exposure to ultrasonic energy.

The label may also allow for the indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, "Practice and Theory of Enzyme Immunoassays," *Laboratory Techniques in Biochemistry and Molecular Biology*" (Burdon, van Knippenberg (eds.), Elsevier, pp. 9–20 (1985)).

The sensitivity of the hybridization assays may be enhanced through the use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q-Beta Replicase systems.

An alternative means for determining the level of expression of the perilipin genes is in situ hybridization. In an in situ hybridization assay cells are fixed to a solid support, typically a glass slide. If DNA is to be probed, the cells are denatured with heat or alkali. The cells are then contacted with a hybridization solution at a moderate temperature to permit annealing of perilipin specific probes that are labelled. The probes are preferably labelled with radioisotopes or fluorescent reporters. In situ hybridization assays are well known and are generally described in Angerer, et al. (*Methods Enzymol.* 152:649–660 (1987)).

Being that multiple perilipin proteins may be present in a single biological sample, it may be desirable to detect the presence of one particular perilipin protein over the others. By comparing their nucleic acid sequences, one can develop species-specific probes useful for differentiating between the various perilipin proteins. It will be understood by those of skill that the length of the species-specific probes can vary significantly. Full length nucleic acid probes can be used to detect the perilipin protein of interest. Alternatively, shorter nucleic acid probes, corresponding to subsequences of the full length nucleic acid sequence, can also be used to selectively detect a particular perilipin protein.

For example, if rat perilipin A is to be detected, the following probe can be used: CACTATGTCCCGCTTC-CCAGGCTG (Sequence I.D. No. 7). This probe will specifically hybridize to rat perilipin A mRNA, but not to rat perilipin B mRNA. Although this sequence is present in rat perilipin B mRNA, it is interrupted in the exact middle with ~800 nt of B-specific sequence. Appropriate hybridization conditions for selectively or specifically detecting perilipin A over perilipin B using the probe corresponding to Sequence I.D. No. 7 are as follows: 5×SSC at ~70° C.

If rat perilipin B is to be selectively detected, the following probe can be used:

```
                                        (Sequence I.D. No. 8)
GTAAGTCCTGCCCCAGGGCCACCTTCTGACTCCCAAGGTAGATTT

GACTGAAGGAGATATAGACCCCCTTTTATCCAGTCCCTGGGCCCA

GAACCTTCTTATACACTGATCTTCCCCAGCCCAAAGTGCAAATGT

TCACAGCCCTGACCTCAGACCTCCCCTCTCCTAGCCCCTAGCCCC

CACCCTCCGACTTGTGCCTCCCACTCGATGATAGAATCATTTGTG

AGTCTCTAGTGGCTCAGACTCCGGCCTCAGATCCTGGAGGAAGGG

CCTGGTAAATTTACATGCCACTGTTCAATAGGCTTTCATGGCACC

TTGAACAGCAGGCTATACATCTGGGGACAGCAGCTGGCCCTATGT

CACCAACAGGGAAAAAAAAAAAAAAAATCAGACTTTT.
```

This sequence, i.e., Sequence I.D. No. 8, begins after the point of divergence between rat perilipin A and rat perilipin B. This sequence will only hybridize to rat perilipin B mRNA, but not to rat perilipin A mRNA. Typical hybridization conditions for use with this probe are as follows: 50% fonnamide; 3×SSC; 0.12M sodium phosphate pH 6.8 at 37° C. As previously mentioned, 1×SSC is defined as 0.15 M NaCl; 0.015 M sodium citrate, pH 7.

If human perilipin is to be selectively detected, one can use the entire human perilipin sequence or, alternatively, one can use the following shorter sequence:

```
                                        (Sequence I.D. No. 9)
TACCCTGGCTGCACAGCCTCGCAGCCGCCCAGGAGGAGGATCATG

AGGACCAGACAGACACGGAGGGAGAGGACACGGAGGAGGAGGA

AGAATTGGAGACTGAGGAGAACAAGTTCAGTGAGGTAGCAGCCC

TGCCAGGCCCTCGAGGCCTCCTGGGTGGTGTGGCACATACCCTGC
```

```
-continued
AGAAGACCCTCCAGACCACCATCTCGGCTGTGACATGGGCACCTG

CAGCTGTGCTGGGCATGGCAGGGAGGGTGCTGCACCTCACACCAG

CCCCTGCTGTCTCCTCAACCAAGGGGAGGGCCATGTCCCTATCAG

ATGCCCTGAAGGGCGTTACTGACAACGTGGTGGACACAGTGGTGC

ATTACGTGCCGCTCCCCAGGCTGTCGCTGATGGAGCCCGAGAGCG

AATTC.
```

This 407 bp sequence will specifically hybridize to the human perilipin protein. Moreover, the above sequence does not possess any of the sequences corresponding to the ADRP region which could potentially detect non-perilipin sequences. As such, the probe corresponding to Sequence I.D. No. 9 is specific for the human perilipin protein.

Alternatively, an oligonucleotide probe specific for human perilipin is as follows: GAATIGGAGACTGAG-GAGAACAA (Sequence I.D. No. 10). The equivalent sequence in rat would be GAAGAAGAagagtcagaGGC-CGAGGAGAACGT (Sequence I.D. No. 11). It should be noted that the rat sequence includes 9 nucleotides (in lower case) that are absent in the human sequence. In addition there are 7 mismatches of the other 23 bp. Hybridization in 5×SSC at ~60° C. will discriminate the human perilipin protein from the rat perilipin protein.

Moreover, hybridization using a probe corresponding to the nucleotide region common to both rat perilipin A and B in 50% formamide; 3×SSC; 0.12M sodium phosphate, pH 6.8 at 37° C. will recognize both the human and rat perilipin cDNAs. However, if the blots are washed in this same buffer at ~55° C., only the rat-rat perilipin hybridization will be stable. The rat-human perilipin hybridization will be washed off the blot. Similarly, based upon sequence information for the human perilipin, hybridization of the human sequence in 50% formamide; 3×SSC; 0. 12M sodium phosphate, pH 6.8 at 37° C. will recognize both human and rat cDNAs, but after washing in this same buffer at ~55° C., only the human-human hybridization will be detected. As such, by varying the hybridization conditions used, one of skill can selectively detect either the rat perilipin protein or the human perilipin protein.

2. Measurement of Perilipin Proteins and Antibodies to Perilipin

In addition to the detection of the perilipin genes or the perilipin gene expressions using nucleic acid hybridization technology, one can use immunoassays to detect either the products of the perilipin genes or the presence of antibodies to the perilipins. Immunoassays can be used to qualitatively or quantitatively analyze perilipin proteins or perilipin antibodies. A general overview of the applicable technology can be found in Harlow and Lane, *Antibodies: A Laboratory Manual* (Cold Spring Harbor Pubs., N.Y. (1988)), incorporated herein by reference.

a. Antibody Production

A number of immunogens may be used to produce antibodies specifically reactive with perilipin antigen. Recombinant perilipin proteins are the preferred immunogens for the production of monoclonal or polyclonal antibodies. Naturally occurring perilipin proteins may also be used either in pure or impure form. Synthetic peptides made using the perilipin protein sequences described herein (i.e., Sequence I.D. Nos. 2, 4 and 6) may also be used as an immunogen for the production of antibodies to the perilipin proteins.

Preferentially, recombinant pezilipin protein or, a fragment thereof, is expressed in bacterial cells as described above, and purified as generally described above and in the examples. The product is then injected into an animal capable of producing antibodies. Either monoclonal or polyclonal antibodies may be generated, for subsequent use in immunoassays to measure the perilipin protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the perilipin protein. When appropriately high titers of antibody to the immunogen are obtained, blood is collected from the animal and antisera is prepared. Further fractionation of the antisera to enrich for antibodies reactive to the perilipin proteins can be done if desired. (See, Harlow and Lane, supra.)

Monoclonal antibodies can be obtained by various techniques familiar to those skilled in the art. Briefly, spleen cells from an animal immunized with a desired antigen are immortalized, commonly by fusion with a myeloma cell (See, e.g., Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Either monoclonal or polyclonal antibodies specific for the gene product can be used in various immunoassays. Such assays include, for example, EUISA, competitive immunoassays, radioimmunoassays, Western blots, indirect immunofluorescent assays and the like.

The invention will now be described in greater detail by way of specific examples. The following examples are offered for illustrative purposes, and are intended neither to limit the invention in any manner.

EXAMPLES

The following protocols and experimental details are referenced in the examples that follow:

Cells and Animals

Male Sprague Dawley Rats (~200 g; Taconic Farms) were used for all animal studies. Murine 3T3-L1 pre-adipocytes were grown to confluence in Dulbecco's Modified Eagle's medium with 10% fetal calf serum. Adipocyte differentiation was initiated with 0.5 mM 3-isobutyl-1-methylxanthine and 0.1 $\mu$M dexamethasone for two days. Subsequently, the cells were incubated with 1 $\mu$M insulin for an additional two days, and thereafter maintained without hormones. The medium was changed every other day. More than 95% of the cells acquired numerous, small lipid droplets within 5 days after confluence and prominent droplets by 10 days.

Cell Preparation. Incubations, and Subcellular Fractionation

Adipocytes were isolated from the epididymal fat pads of 180–200 g male rats fed. ad libitum with standard National Institutes of Health chow. The fat pads were digested with collagenase, and cells were isolated according to the method of Rodbell, *J. Biol. Chem.* 239:375–380 (1964). All incubations were carried out in Krebs-Ringer buffer, pH 7.4, supplemented with 30 mM HEPES (KRH). Adenosine, at 200 nM, was included to suppress cAMP production and stimulation of cAMP-dependent protein kinase activity (Honnor, et al., *J. Biol. Chem.* 260:15122–15129 (1985)). Removal of both endogenous and exogenous adenosine was achieved with 0.5 units/ml adenosine deaminase.

$^{32}$P Loading and Incubation of Adipocytes

For the experiments depicted herein, the fat cakes were obtained from incubations performed as follows. Isolated adipocytes were washed twice in 5% BSA-KRH medium with reduced phosphate concentration (100 $\mu$m), suspended in the same medium at 20–25% packed cell volume/ml (v/v), and loaded with 125 $\mu$Ci/ml of $^{32}$P, at 37° C. for 90 min before addition of hormones and other agents, as described in the figure legends. After hormone treatment, at 37° C., the cells were centrifuged through dinonylphthalate; the medium and dinonylphthalate under the cell pellet were aspirated and discarded. Immediately, the cells were homogenized in 20 mm Tris-HCl, pH 7.4, 255 mm sucrose, 10 mM NaF, 10 mm NAPP$_1$, 200 $\mu$l m sodium orthovanadate, 1 mM EDTA, 10 $\mu$g/ml leupeptin, 1 mM benzamidine and 0.1 $\mu$M phenylmethylsulfonyl fluoride that had been equilibrated at 18° C. Each ml of fat cells was homogenized in 5 ml of medium, and subcellular fractions were prepared as described previously (Simpson, et al., *Anal. Biochem.* 119:424–427 (1982)). Subcellular fractionations were carried out at 4° C.

Extraction of Fat Cake

The isolated fat cake fraction was suspended in an equal volume of an extraction medium containing 1% SDS, 1 mM EDTA, 20 $\mu$m leupeptin, 1 mM benzamidine, and 20 mM NaF. The mixture was warmed to 37° C., mixed vigorously, and immersed briefly in a bath sonicator. After centrifugation at 2,000 rpm in a Sorvall GLC-1 desk top centrifuge at room temperature, the infranate was withdrawn and stored at −80° C. This procedure was found to separate >90% of all proteins from the lipid in the fat cake.

Preparation of 62-kDa Phosphoprotein and Antibody Production

Extracted fat cake proteins from $^{32}$P-loaded adipocytes were separated by SDS-PAGE in gels containing 10% acrylamide, 0.07% N,N'-methylene bisacrylamide, a system that effectively separates polypeptides in the 60-kDa to 70-kDa range. Approximately 4 $\mu$g of the 62-kDa protein from $^{32}$P-loaded cells were subjected to SDS-PAGE and transferred to nitrocellulose. A nitrocellulose strip containing the protein was excised, dissolved in dimethyl sulfoxide, and mixed with Freund's complete adjuvant just prior to injection into rabbits. Subsequent boosts were performed with 1-$\mu$g injections of protein that was eluted directly from gel chips.

Immunoaffinity Purification of Anti-62-kDa Antiserum

Approximately 10 $\mu$g of the 62-kDa protein in 10 lanes of an SDS-PAGE slab gel were transferred to nitrocellulose. A strip containing the 62-kDa protein was excised and blocked in 50 mM, Tris-HCl, pH 7.5 160 mM NaCl, and 0.05% Nonidet P-40 (TBS-NP40) containing 4% dry milk. The strips were incubated in 5 ml with a 1:25 dilution of anti-62-kDa serum (CL5) in TBS-NP40 with 4% dry milk for 2 h, washed three times in TS-NP40, and eluted with 4.5 ml of 100 mM glycine, pH 2.5. The eluted antibody was neutralized with Tris base and stored at −80° C.

Western Blotting

For Western blotting, proteins were separated by SDS-PAGE, transferred to nitrocellulose, and blocked with 4% dry milk in TBS-NP40. Routinely, strips containing the 62/65/67-kDa proteins were incubated with 1:500 dilution of the CL5 antiserum or a 1:20 dilution of immune-purified antibodies prepared as described above. Immunoreactivity was visualized with alkaline phosphatase-linked goat anti-rabbit IgG and the BCIP/NTB staining procedure (Bio-Rad).

Culturing Cells and Immunofluorescence Detection of Proteins in 3T3-L1 Adigocytes 3T3-L1 mouse embryo fibroblasts (ATCC # CCL 92.1 3T3-L1 (CL 173), American Type Culture Collection) were cultured Dulbecco's modified Eagle's medium (25 mM glucose; GIBCO) supplemented with 10% fetal bovine serum (Inovar), 8 $\mu$g/ml biotin, and 4 1 $\mu$g/ml pantothenic acid. Cells were seeded at a density of 1×10$^5$ cells/well in culture chamber slides (Lab-Tek) and maintained at 37° C. in a 95% air/5% $CO_2$ atmosphere; the medium was changed at 48-h intervals. Two days after reaching confluence, the cells were stimulated to differentiate into adipocytes by addition of 100 nM dexamethasone (Rubin, et al., *J.Biol. Chem.* 253:7570–7578 (1978)) for 2 days. Subsequently, the cultures were incubated with 10 $\mu$g/ml insulin and taken for microscopic studies upon appearance of lipid droplets.

Two hours prior to the experiment, cells grown on the double well plastic slides were washed first with medium and then with phosphate-buffered saline (PBS, pH 7.4) before fixation in 3% (w/v) paraformaldehyde in PBS for 30 min. After an additional wash in PBS, the cells were incubated in PBS, 1.5 mg/ml glycine (to quench aldehydes), 1.5 mg/ml goat IgG, and 0.1% saponin for 60 min before immunolabelling with a double labeling procedure. The fixed cells were incubated with either a 1:50 dilution of rabbit antiserum to the 62-kDa protein or undiluted affinity-purified antibodies prepared as described above. Cells incubated with the antiserum were incubated subsequently with a 1:50 dilution of dichlorotriazinylaminofluorescein-labeled goat anti-rabbit IgG (Jackson Immunoresearch), whereas the cells incubated with the purified antibodies were incubated subsequently with peroxidase-labeled goat anti-rabbit IgG (Jackson Immunoresearch), again at a 1:50 dilution. Incubations with both primary and secondary antibodies were for 1 h at room temperature on a shaker in a moist chamber. After a final wash, fluorescent immunolabelled cells were mounted in p-phenylenediamine glycerol (Johnson, et al., *J. Immunol. Methods* 43:349–350 (1981)) and visualized with a Leitz Microscope using a ×25 or ×50 oil objective and fluorescence or phase microscopy. Cells immunolabelled with peroxidase-conjugated second antibodies were processed further, including refixation in glutaraldehyde and subsequent reaction with diaminobenzene and reduced osmium to render reaction products opaque (Graham, et al., *J. Histochem. Cytochem.* 4:291–303 (1966)). Cells were dehydrated in alcohol, embedded in resin, and visualized with brightfield and phase optics either as whole amounts or in 1-$\mu$m sections.

Perilipin Peptide Sequences

Rat epididymal adipocytes were isolated, incubated with [$^{32}$P]-orthophosphate and homogenized to prepare fat cakes as described above. Proteins were extracted from the fat cake with SDS and separated by SDS-PAGE; the 62-kDa phospho-variant of perilipin was located by wet gel autoradiography and excised. The gel chip was minced and protein was eluted by two sequential incubations at 37° C. in 20 Mm Tris-HCl, pH 7.8, 5 $\mu$g/ml leupeptin, 0.1 mM benzamidine, and 1 mM EDTA for 8 hr. The eluates were concentrated using a Centricon-10 cartridge (Amicon) and the SDS concentration was reduced by repeated dilution and concentration using Centricon-10; SDS concentration was measured colorimetrically with the BioRad protein assay kit. Perilipin recovery was quantitative and the SDS concentration was reduced to <0.02%. For peptide analysis, 5 pg of perilipin was digested to completion with 0.2 jug trypsin for 2 hr at 37° C. in 2OmM Tris-HCl, pH 7.8, 0.5 mM $CaCl_2$.

After centrifugal ultrafiltration of the digest using a Centricon-10 cartridge, the filtrate was treated sequentially with KCl and guanidine (Prussak, et al., *Anal. Biochem.* 178:233–238 (1989)). To remove residual traces of SDS, the filtrate was applied to a 2.1×250 mm Vydac 214TP column equilibrated with 0.1% trifluoroacetic acid (TFA). A Hewlett-Packard Model 1090 M HPLC with a column oven (60° C.) was used for peptide separations. The column was washed with 0.1% TFA for 10 min at 250 $\mu$l/min. The flow rate was reduced to 150 Allmin and peptides were eluted with 0.085% TFA in acetonitrile (Stone, et al., *J. Chromat.* 359:203–212 (1986)). The column effluent was monitored at 280 nm and fractions were collected manually, immediately placed on dry ice, and stored at −80° C. Several of the peak fractions were subjected to another separation on an Applied Biosystems 250×1 mm Aquapore RP-300 column; the flow rate was 100 $\mu$l/min with a 0–100% gradient of acetonitrile over 30 min. The homogeneous peptides thus obtained were analyzed with an Applied Biosystems Model 477A sequencer equipped with a Model 120A PTH Analyzer. Initially, the Normal-1 cycles were used, but the modifications re commended by Tempst and Riviere (*Anal. Biochem.* 183:290–300 (1989)) and Speicher (See, Speicher, in *Techniques in Protein Chemistry* (T. Hgli (Ed.), Acade mic Press, San Diego, pp 24–35 (1989))) were incorporated for the majority of the studies. Data analyses were aided by the Applied Biosystems Model 610A software.

Phosphoamino Acid Analysis $^{32}$P-labelled 62-kDa and 65/67-kDa forms of perilipin were purified from quiescent and stimulated celbs, respectively, as described above. Phosphoamino acids were determined according to Cooper, et al (*Meth. Enzymol.* 99:387–402 (1983).

RNA Isolation and Gel Analysis

RNA was isolated from rat and human primary adipocytes and from 3T3-L1 pre-adipocytes and adipocytes by phenol extraction (Kimmel, *Develop. Biol.* 122:163–171 (1987)). To ensure complete solubilization of lipid, aqueous-SDS to cell pellet volumes were >3:1. RNA from brown fat was from Drs. D. Ricquier and C. Forest, Centre National de la Recherche Scientifique, Meudon-Bellevue, France. RNAs from other tissues were from Dr. C. Roberts, National Institutes of Health, Bethesda, Md. RNA was separated by denaturing gel electrophoresis, blotted onto filters, and hybridized with cDNA probes in 50% formamide-0.8M Na$^+$ at 37° C. (Wahl, et al, *Meth. Enzymol.* 152:572–581 (1987)).

Screening of the cDNA Library

Poly (A)$^+$ RNA was prepared from rat adipocytes and used to construct a lambda gt11 cDNA library (Kimmel, et al., *Meth. Enzymol.* 152:307–316 (1987)). The library was screened initially with total and affinity-purified polyclonal antiserum against 62-kDa perilipin (Klein, et al., *Science* 241:1467–1472 (1988)). Three overlapping clones were selected from an initial screen of 100,000 recombinants. Inserts were subeloned into plasmids and sequenced using the dideoxynucleotide chain termination method as applied to double stranded DNA (Sanger, et al., *Proc. Natl. Acad. Sci.* 74:5463–5467 (1977)). Labelled inserts from these clones were used to rescreen the cDNA library.

For the cloning of human perieipin, a human adipocyte cDNA expression library was obtained from Clontech (Palo Alto, Calif.) and positive clones were identified by hybridization using a full length cDNA probe based on rat perilipin A (See, Sequence I.D. No. 1). Hereinafter, the methodology used is the same as that used for the cloning of the rat perilipin proteins A and B.

Polymerase Chain Reaction (PCR)

The GENEAMP RNA PCR Kit (Perkin Elmer-Cetus) was used for reverse transcription-coupled/PCR (i.e., RT-PCR)

amplification of RNA sequences. Oligonucleotides were prepared with an Applied Biosystems synthesizer.

Databank Search

The nucleic acid and derived amino acid sequences of the perilipin cDNAs were compared to known sequences using searches by BLAST (Altschul, et al., *J. Mol. Biol.* 215:403–410 (1990)) and FASTA (Pearson, et al., *Proc. Natl. Acad. Sci.* 85:2444–2448 (1988)) algorithms; Prosite (Pearson, et al., *Proc. Natl. Acad. Sci.* 85:2444–2448 (1988)) was used for relevant structure and domain analyses based on primary amino acid sequences.

EXAMPLE I

Protein Analyses

Figure 1:
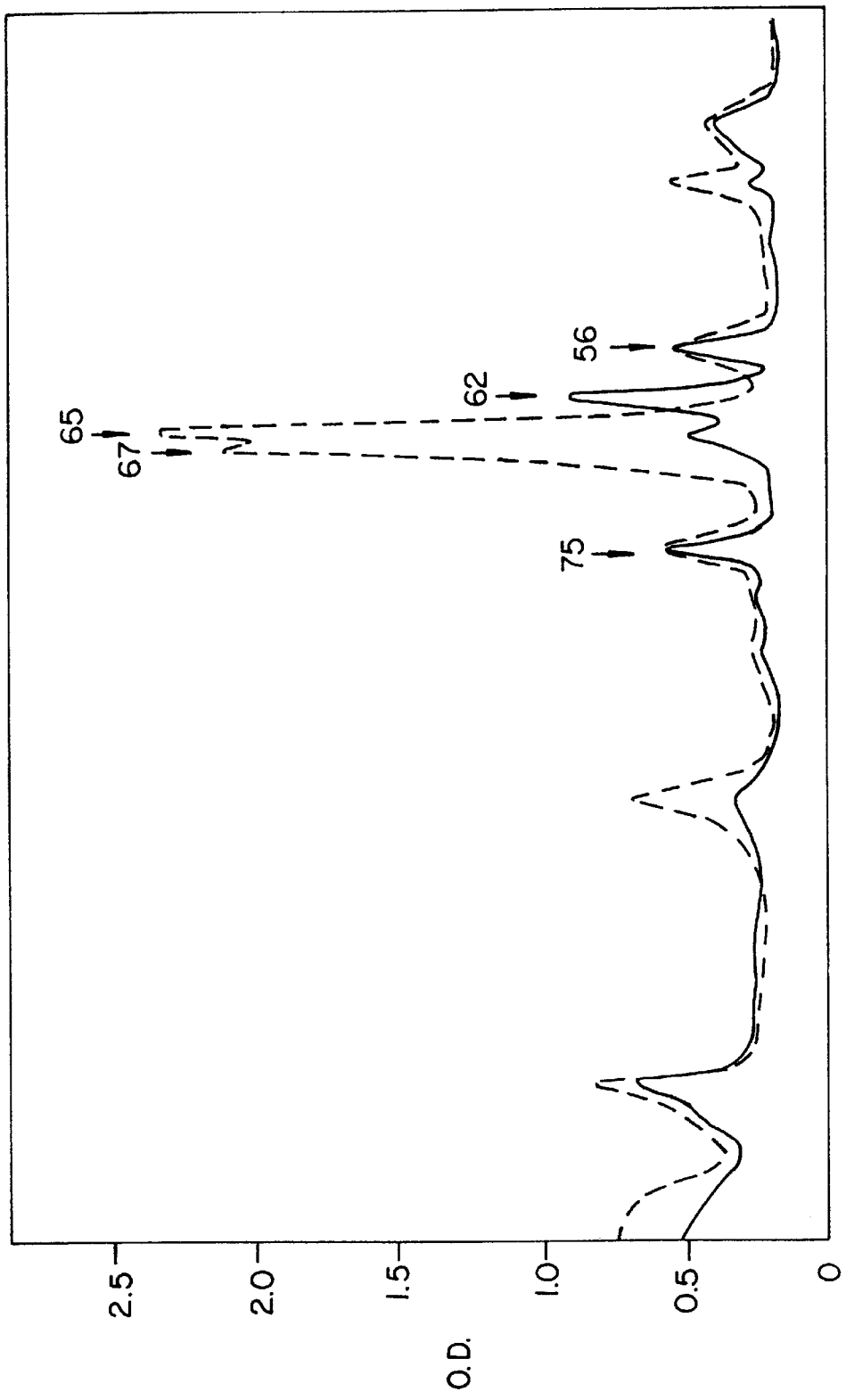
FIG. 1. Densitometric scan of adipocyte phosphoproteins. Isolated adipose cells (10%, v/v) were incubated for 2.5 h with 10 $\mu$Ci/ml $^{32}$p, (50 $\mu$M P$_1$) in the presence of 25 nM PIA and 1% BSA. Control cells () received no further treatment, and stimulated cells (- - - -) received 10 $\mu$M isoproterenol for 5 min. Aliquots (200 $\mu$l), containing 20 $\mu$l of packed cells were added to 400-$\mu$l Brinkman centrifuge tubes containing 100 $\mu$l of dinonylphthalate and centrifuged immediately for 15 s in a Beckman/Spinco 152 Microfuge. The tubes were cut with a razor blade just below the cell layer and the cells were lysed in 100 $\mu$l of 20% SDS. Fifty p1 of the lysates in Laemmli sample buffer maintained at 20% SDS were processed through SDS-PAGE. The exposed autoradiograms were scanned on a Molecular Dynamics Scanning Densitometer. The arrow points to Molecular Weight estimations (kDa).

The major phosphoprotein(s) found in adipose cells upon stimulation with the β-adrenergic agonist, isoproterenol, and elevation of A-kinase activity is a doublet that migrates at 65/67-kDa upon SDS-PAGE (FIG. 1). Previously, it was demonstrated with in vitro phosphorylation studies that the 67-kDa phosphoprotein was derived from the 65-kDa species upon further phosphorylation with A-kinase (Egan, et al. (1990) *J. Biol. Chem.* 265, 18769–18775). Concomitant with the appearance of the 65/67-kDa phosphoprotein is the disappearance of a 62-kDa species, a major phosphoprotein which is constitutively phosphorylated in unstimulated cells (FIG. 1). As shown below, the 65/67-kDa doublet is derived from the 62-kDa protein upon phosphorylation by A-kinase, and it is apparent that the doublet is by far the most abundant radiolabelled phosphoprotein in the cell. Under the incubation conditions, steady-state incorporations of $^{32}p$ into the γ-phosphate of cellular ATP is achieved 60–90 min after introduction of [$^{32}P$]orthophosphate, and steady-state phosphorylation of the 62-kDa species requires approximately 90–120 min. In adipocytes labeled to apparent isotopic equilibrium with $32P_i$, the ratio of $^{32}P$ in the 65/67-kDa phosphoprotein of stimulated cells to that in the 62-kDa protein of unstimulated cells is approximately 5:1, as determined by scanning densitometry and by cutting and counting of SDS-PAGE gels.

FIG. 2 shows the distribution among gross adipocyte homogenate fractions (supernate, membrane, and fat cake) of proteins by silver staining and of major phosphoproteins by autoradiography. Isoproterenol-stimulated cells are compared to control cells in which the A-kinase was maintained in an inhibited state by inclusion of PIA, an agonist of the adenosine receptor that inhibits adenylyl cyclase and, thus, cAMP formation, (Honnor, et al., *J. Biol. Chem.* 260:15122–15129 (1985)). The abundant protein at 68-kDa by silver staining is bovine serum albumin carried over from the cell incubation medium. Both the 62-kDa and the 65/67-kDa phosphoproteins are found predominantly with the fat fraction, and the disappearance of the 62-kDa species upon isoproterenol stimulation is again evident. Scanning densitometry reveals that the fat fraction contained <15% of the total homogenate protein, mostly contamination by proteins that fractionate primarily with the membranes or supernate (FIG. 2A). Thus, association of the 62-kDa and 65/67-kDa phosphoproteins with the fat cake distinguishes this protein(s) from most others. Two additional phosphoproteins, presumably A-kinase substrates, are located primarily, if not exclusively, with the fat derived from isoproterenol-stimulated cells. These are the 46-kDa protein (i.e., perilipin B) and the 84-kDa protein, which has been identified by Western blotting as hormone-sensitive lipase, the rate-limiting enzyme of lipolysis.

The 62-kDa phosphoprotein from unstimulated adipocytes is sufficiently abundant to be seen by either silver (FIG. 3A) or Coomassie Blue staining (FIG. 3B) of crude extracts of the lipid fraction. As seen in FIG. 3A, upon stimulation with isoproterenol the 62-kDa protein is reduced considerably and proteins of 65-kDa and 67-kDa appear, the latter a more diffuse band below the contaminating 68-kDa BSA, reduced in this example by washing cells free of most BSA prior to stimulation and homogenization. FIG. 3 shows that the changes in phosphoprotein composition under the two cell incubation conditions correspond precisely to the changes as revealed by staining, a finding consistent with the notion that the 65/67-kDa protein is derived from the 62-kDa species. With BSA as a standard, it was determined by silver staining that the fat cake from epididymal adipose cells of a 180–200-g rat contains approximately 5 μg of this protein or approximately 0.25–0.5% of the total protein. However, this may be an underestimation of its abundance; relative to other proteins the phosphoprotein stains poorly with silver as compared with Coomassie Blue (cf., FIGS. 3, A and B).

Figure 4A:
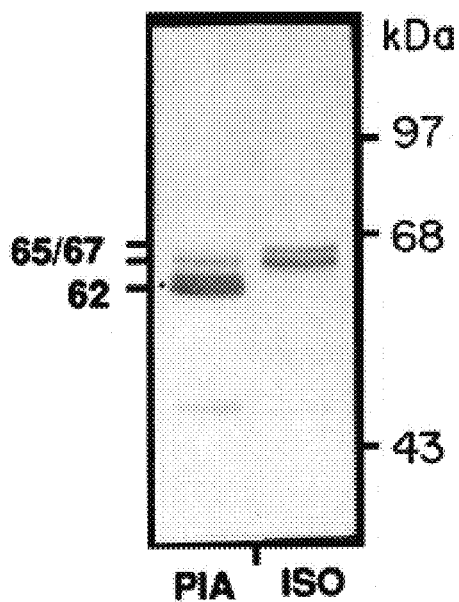
FIGS. 4A–D. Recognition of 65/67-kDa phosphoproteins from stimulated adipocytes by antibodies against the 62-kDa phosphoprotein from unstimulated cells. The figure shows a Western blot and autoradiogram from lipid extracts of control (PIA) and isoproterenol-stimulated (ISO) $^{32}$P-loaded adipocytes. Blotting was performed with affmity-purified antibodies against rat adipocyte 62-kDa phosphoprotein isolated from fat cakes. A, Western blot; B, autoradiogram. Aliquots of lipid extracts from a separate cellular experiment (C and D) were incubated for 1 h at 37° C. with the indicated concentrations of bovine intestinal mucosal alkine phosphatase (Sigma, Type VII-L) in 13 mM Tris-HCl, pH 8. The final concentration of SDS carried over from the lipid extract medium to the alkaline phosphatase reaction mixture was 0.14%. Each lane contained 1/50 of the lipid extract from a single rat, i.e., approximately 100 ng of the 62- or the 65/67-kDa phosphoprotein. In the unstimulated (PIA) sample, the heavily labeled phosphoprotein (marked by arrow) in the autoradiogram (D) corresponds to the upper band (also marked by arrow) of the prominent doublet in the Western blot (C); both migrated at 62-kDa in SDS-PAGE. The lower band of this doublet contained no $^{32}$P Note that following phosphatase treatment and dephosphorylation, immunoreactive material was found only at the position of this lower band of the doublet. Note also that A and B show a band at approximately 46-kDa that was determined to be perilipin B.
Figure 4B:
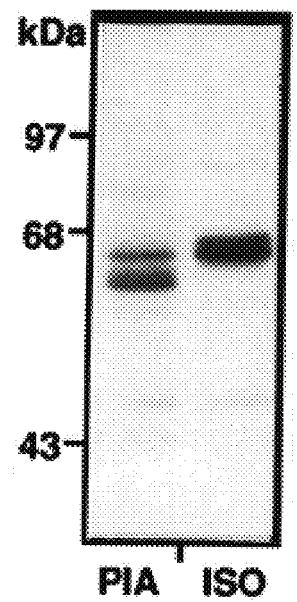
Figure 4C:
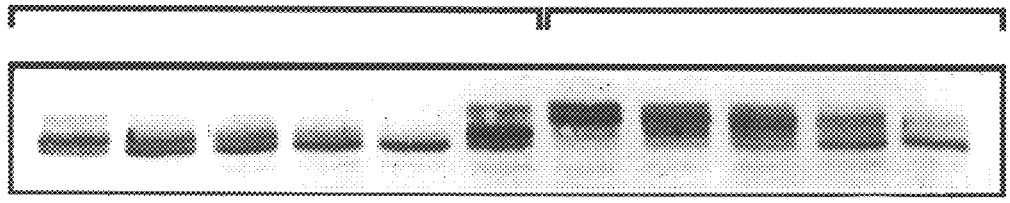
Figure 4D:
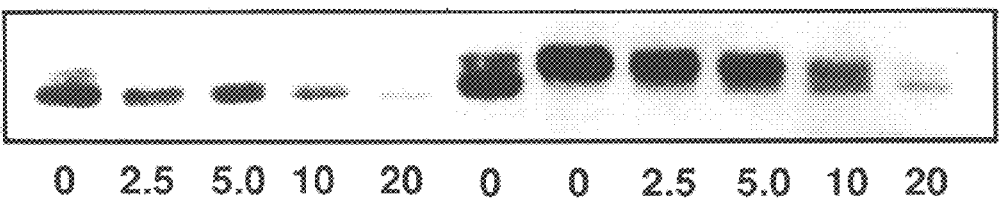

Polyclonal antiserum was raised in rabbits against the 62-kDa protein from unstimulated cells, and antibodies against the 62-kDa species were immunopurified. These affinity-purified antibodies recognize both 62- and 65-kDa proteins in unstimulated cells, but react with 65- and 67-kDa proteins in isoproterenol-stimulated cells (FIG. 4A). Identical results were obtained with three different unpurified polyclonal antisera against the 62-kDa species. These data provide further evidence that the various species of phosphoprotein in this region are phosphorylation variants of a single polypeptide, a conclusion buttressed by phosphatase studies (FIGS. 4, C and D). Following their dephosphorylation (FIG. 4D) by alkaline phosphatase, all species of the proteins in question migrate identically in SDS-PAGE as a 60–61-kDa polypeptide as shown by immunoblotting (FIG. 4C; see legend to FIG. 4). Moreover, in the control (i.e., unstimulated) cells, a significant fraction of the protein migrates as a 60–61-kDa unphosphorylated species, but the relative distribution between the phospho and dephospho forms was variable among different cell preparations.

The disappearance of the 62-kDa form upon isoproterenol stimulation of cells indicates that the protein undergoes quantitative phosphorylation in vivo. However, both Western blotting (FIG. 4) and autoradiography (FIG. 3) indicate that a fraction of the protein persists in an ~65-kDa form despite the presence of 25 mM PIA, a concentration sufficient to suppress A-kinase activity (Honnor, et al, *J. Biol. Chem.* 260:15122–15129 (1985)).

This 62-kDa perilipin protein is also found in murine 3T3-L1 adipocytes, and its behavior in SDS-PAGE upon stimulation with isoproterenol is identical to that seen in the rat adipocytes. In $^{32}P$-loaded 3T3-L1 adipocytes, as in the mature rat adipocytes, the 62- and 65-kDa species are the most prominent phosphoprotein in control and stimulated cultured adipocytes, respectively. On the other hand, the undifferentiated 3T3-L1 fibroblasts, whether stimulated or inhibited, contain no readily detectable phosphoprotein at 62 or 65-kDa.

Moreover, it has been found that the 62-kDa protein and its more highly phosphorylated 65/67-kDa forms are highly insoluble. The protein exhibits a strong propensity to aggregate in the absence of detergent and once aggregated cannot be redissolved in a variety of organic solvents nor in laemmli SDS sample buffer. However, the protein remains in solution if the SDS concentration is maintained at 0.01% or greater. Since these properties are reminiscent of intermediate filament proteins, such as vimentin, which as noted above has been reported to surround the lipid droplet (Franke, et al.

Figure 5A:
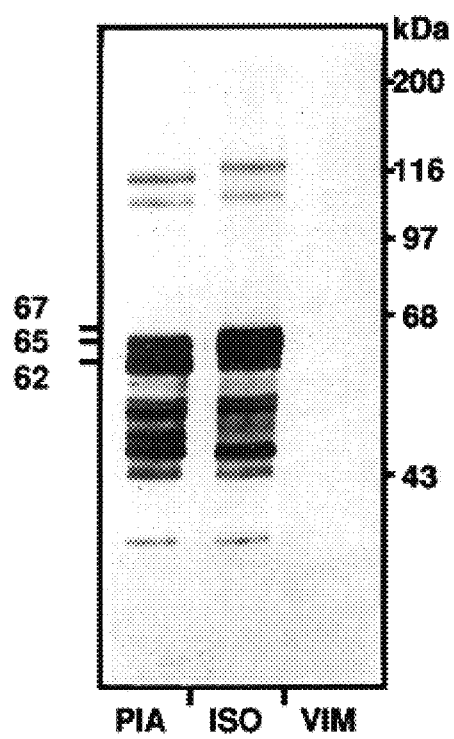
FIGS. 5A & B. Western blotting of extracted adipocyte lipid fractions with polyclonal anti-62-kDa and anti-vimentin antisera. Adipocytes were isolated and treated as described in FIG. 1, and lipid extractions were performed. Aliquots of extracts from unstimulated (PIA) and isoproterenol-stimulated (ISO) cells were processed through SDS-PAGE, transferred to nitrocellulose, and incubated with anti-62-kDa serum (A) or anti-vimentin antiserum (B). The anti-62-kDa serum used in this experiment was not immunoaffinity purified. The 3rd lane in each blot contained 180 ng of vimentin (VIM).
Figure 5B:
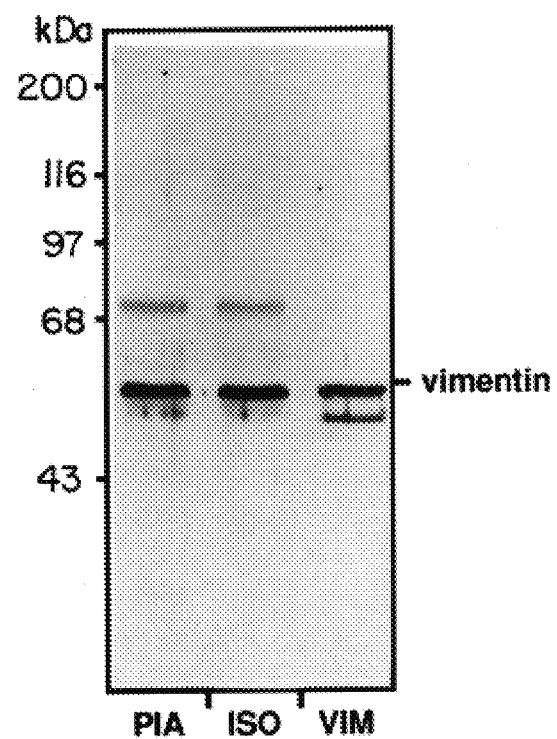
Figure 6A:
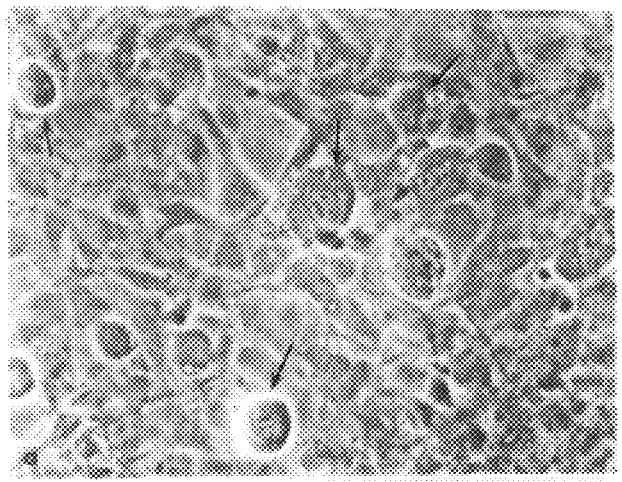
FIGS. 6A–E. Immunocytochemical detection of the 62-kDa protein surrounding the lipid storage droplets in 3T3-L1 adipocytes. a, b, and c, cultured differentiated 3T3-L1 adipocytes immunolabelled with anti-62-kDa antiserum and dichlorotriazinylaminofluorescein-labeled second antibodies. Rounded 3T3-L1 cells contain lipid droplets apparent as lucent spheres with phase optics (a, at arrows) and immunofluorescent staining in association with lipid droplets (b, at arrows). At higher magnification (c) the immunofluorescent staining is visualized as rings in association with the periphery of lipid droplets of various sizes, a and b, ×210; c, ×680. d and e, cells were immunolabelled with affinty-purified anti-62-kDa antibodies and peroxidase-conjugated second antibodies. Immunoperoxidase staining surrounding the periphery of intracellular lipid droplets can be seen clearly in 1-μm resin-embedded sections with brightfield (d) and phase microscopy (e). Other more elongate cells in the culture, without lipid droplets, are not immunolabelled, d and e, ×525.
Figure 6B:
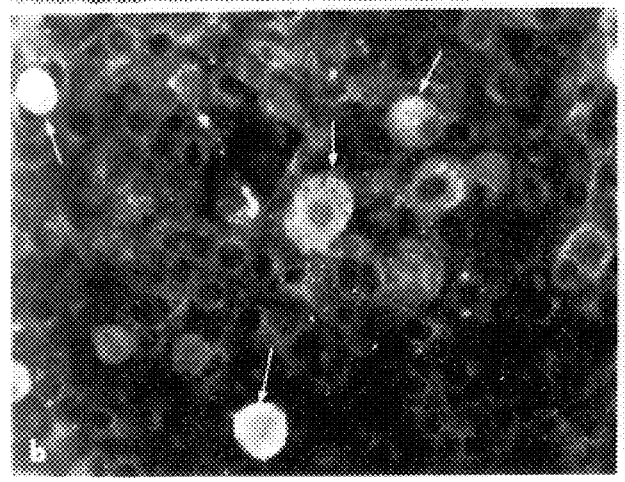
Figure 6C:
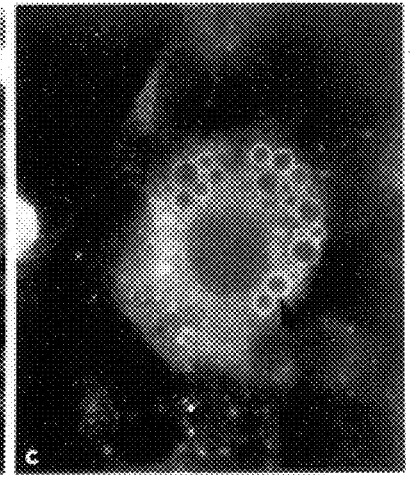
Figure 6D:
Figure 6E:

Cell 49:131–141 (1987)), the extracted lipid samples were probed by Western blotting with antisera against both the 62-kDa and vimentin proteins. Indeed, vimentin (molecular mass=55–58-kDa) is associated with the fat cake (FIG. 5B), but the anti-vimentin serum recognizes neither the 62- nor the 65/67-kDa species. Similarly, polyclonal anti-62-kDa serum, which recognizes several different proteins in extracted fat, does not recognize vimentin (FIG. 5). Thus, the phosphoprotein identified is different from vimentin.

Immunocytochemical examination of differentiated 3T3-L1 adipocytes using as primary antibody either antiserum against the 62-kDa protein or affinity-purified antibodies shows similar localization results with secondary antibodies conjugated with either a fluorescent marker or with peroxidase (FIG. 6). Fluorescence (FIG. 6, a–c) and peroxidase (FIG. 6, d and e) labeling was present in strikingly well defined ring-like patterns surrounding both large and small lipid droplets. By focusing at various levels in the cell, intracellular patches of immunofluorescence could be resolved into aggregates of tiny circles, presumably at the periphery of very small lipid droplets. There was no diffuse immunolabelling of the adipocyte cytoplasm nor staining of Golgi with the anti-62-kDa antibodies. Cells in the same culture which contained no visible lipid droplets under phase microscopy also showed no immunofluorescent labeling with the specific antibodies. Similarly, undifferentiated fibroblasts contain no proteins recognized by the antiserum. Finally, the localization of the 62-kDa protein to the lipid droplet periphery is not an artifact of antibody affinity for the lipid surface, since various rabbit antisera, both preimmune and those directed against other adipocyte proteins (e.g., the glucose transporter isoform, Glut4), do not reveal ring-like images such as those seen in FIG. 6.

EXAMPLE II

Isolation of cDNAs

Figure 7:
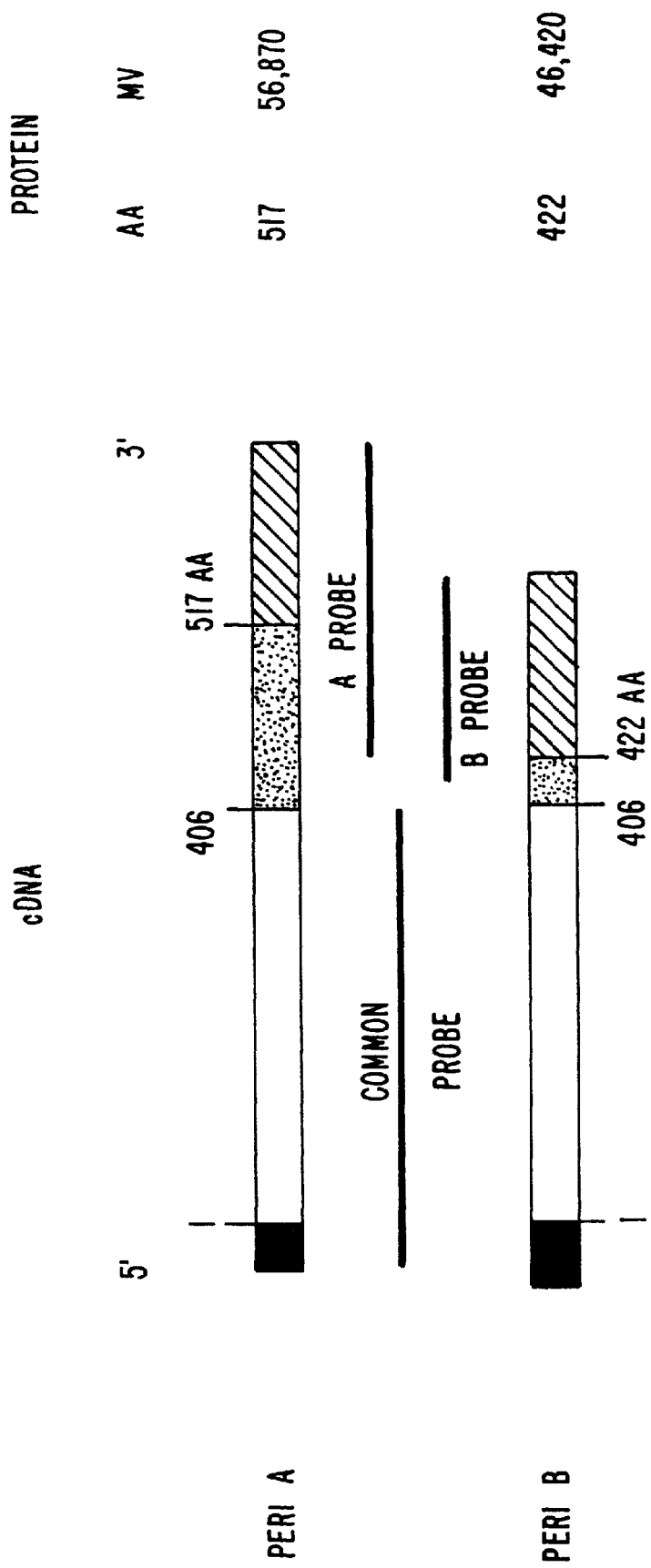
FIGS. 7A & B. Diagram of perilipin A and perilipin B cDNAs from rat primary adipocytes. Black boxes identify 5' untranslated regions. Open boxes represent the open reading frame common to both A and B cDNAs. Stippled areas are open reading frame sequences that are specific to either perilipin A or B. The striped regions are 3'-untranslated sequences unique to A or B. Also depicted are the sizes in amino acids (AA) and molecular weights (MW) in Daltons of the predicted translation products. The approximate sizes and positions of the hybridization probes derived from sequences common to both A and B as well as from regions specific to A or B are indicated.

A lambda gt11 rat adipocyte cDNA expression library was constructed and probed with total and affinity-purified polyclonal antiserum to perilipin. The affinity-purified antiserum reacts specifically with perilipin on protein blots. Several cDNAs were identified that encoded epitopes which crossreacted with both antisera. cDNA inserts were subcloned into plasmids and used as probes to re-screen the library to obtain full-length protein-coding recombinants. Two classes of cDNAs (i.e., Sequence I.D. Nos. 1 and 3) were identified that are predicted to encode distinct, but related, proteins (FIG. 7). The two cDNAs are identical both in their 5' untranslated regions and in the first 1218 nucleotides (406 amino acids) of their protein coding regions; beyond, they diverge. One, perilipin A, is predicted to encode a protein of 517 amino acids, and the other, perilipin B, a protein of 422 amino acids.

The predicted protein sequence of perilipin A (Sequence I.D. No. 2) includes 7 peptides present in purified rat 62-kDa perilipin; the predicted molecular weight, 56,870 Da, is similar to the ~60,000 Da size of dephosphorylated perilipin. Perilipin A possesses six consensus A-kinase sites, consistent with the number of phosphates added to perilipin by A-kinase during lipolytic activation of adipocytes (Egan, et al., *J. Biol. Chem.* 265:18769–18775 (1990). Each of the putative A-kinase sites includes serine as the phosphate acceptor, and in further experiments (data not shown) it has been found that only serine residues of the 65/67-kDa perilipin are phosphorylated following the elevation of A-kinase activity in rat adipocytes. By contrast, in unstimulated cells, most radiophosphate of the 62-kDa form of perilipin is on threonine. No phosphotyrosine was detected.

The site of divergence between the perilipin B and perilipin A cDNAs incorporates a consensus donor RNA splice site, GTXXGT (Smith, et al., *Ann. Rev. Gen.* 23:527–577 (1989)), suggesting that alternative RNA splicing gives rise to the two variants. Perilipin B translation terminates after amino acid 422 and is predicted to yield a protein of 46,420 Da, approximately 10.5-kDa smaller than perilipin A. (See, Sequence I.D. No. 4.) Perilipin B contains five of the seven peptide sequences identified in perilipin A and three of the six consensus A-kinase sites.

To isolate the cDNA encoding the human perilipin protein, a human adipocyte cDNA library was obtained from Clontech (Palo Alto, Calif.) and positive clones were identified using a full length cDNA probe based on rat perilipin A (See, Sequence I.D. No. 1). The methodology used to clone human perilipin is similar to that used for the cloning of perilipin A and B. In cloning human perilipin, it has been discovered that the DNA is transcribed into an mRNA of about 3.4 kb which, in turn, encodes a human perilipin protein having an amino acid sequence comprising Sequence I.D. No. 6. It has been determined that amino acids 14 to 421 of the human perilipin protein are 85% identical (95% similar) to amino acids 9 to 419 of perilipin A. It is expected that since the amino acid sequences for perilipin A and B diverge after amino acid 406, the human perilipin protein is a homolog of perilipin A. Moreover, as with both perilipin A and B, the human perilipin protein is expressed in adipocytes.

EXAMPLE III

Perilipin Sequence Analyses

The perilipin nucleic acid and predicted amino acid sequences were analyzed by BLAST and FASTA searches of the GeneBank, EMBL and SwissProt data bases (Altschul, et al., supra., and Pearson, et al., supra.). Only one listing, the mouse differentiation-related protein ADRP, exhibited a significant (p=<0.0003) sequence relationship with perilipin (Jang, et al., *Proc. Natl. Acad. Sci.* 89:7856–7860 (1992)). Amino acids 17 to 121 of perilipin A and B are ~40% identical (~65% similar) in sequence to amino acids 9 to 113 of ADRP. Combined Garnier-Osguthorpe-Robsons (Garnier, *Biochimie* 72:513–524 (1990)) analyses of perilipin amino acid sequences indicated three regions (amino acids 142–157, 247–269, and 348–368) of perilipins A and B with moderately positive hydrophobic indices, although none of these is predicted to form membrane spanning domains as defined by Kyte and Doolittle (Kyte and Doolittle, *J. Mol. Biol.* 157:105–132 (1982)).

Attempts to perform amino terminal sequence analysis of purified perilipin have been unsuccessful, suggesting that the N-terminal amino acid is modified. As yet, no biochemical data exits regarding the presumed blocking group. There are several potential N-myristoylation sites located within the interior of perilipin. However, since the size of perilipin is similar to that predicted from cDNA sequencing, the protein may not be processed in a manner that places any of the putative myristoylation sites at the N-terminus, as is required for the acyl modification (Gordon, *Clin. Res.* 38:517–528 (1990)). The amino acid sequence of perilipin also includes a potential N-glycosylation site (Gavel and von Heijne, *Prot. Eng.* #:433–442 (1990)) at amino acid 42, but apart from potential phosphorylation sites, no additional modifications are predicted and no homologies to known structural domains were identified using Prosite (Bairoch, supra.).

EXAMPLE IV

Multiple Perilipin mRNA Forms in Rat and Murine Adipocytes

Figure 8:
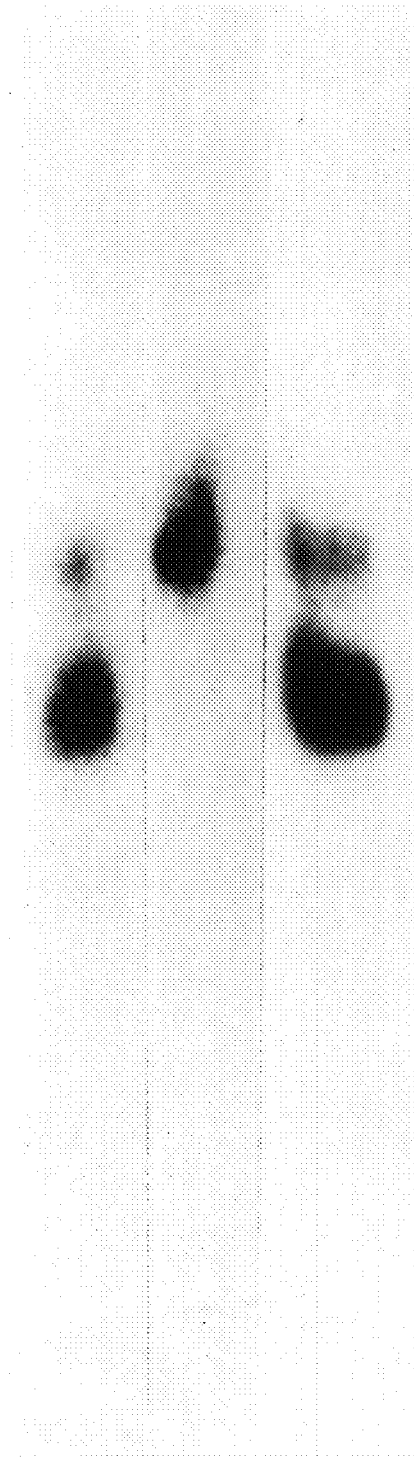
FIGS. 8A–C. Expression of perilipin A and B RNAs. Total RNA was isolated from rat primary adipocytes, separated by electrophoresis on denaturing agarose gels and blotted to nitrocellulose filters. Identical blots were hybridized separately to probes common (C) to A and B or specific to either B or A cDNAs as seen in lanes C, B, and A, respectively (See, FIG. 7).
Figure 9A:
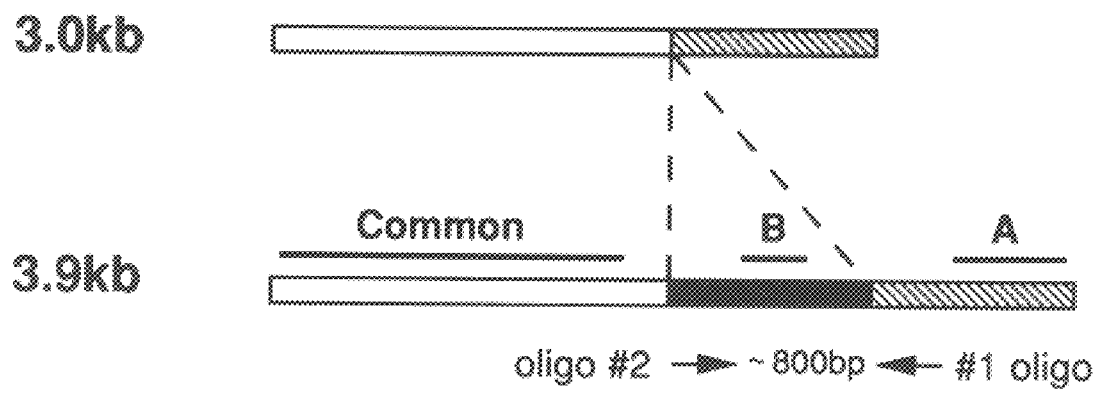
FIGS. 9A & B. Perilipin A and B RNAs arise by differential splicing.

Rat adipocyte RNA blots were hybridized with probes from the region common to perilipins A and B, and from regions unique to the A or B cDNAs (See, FIG. 7). The common C probe recognized two mRNAs of ~3.9 kb and ~3.0 kb. Whereas only the larger, less abundant mRNA was recognized by the B probe, both mRNAs hybridized to the A probe (FIG. 8). Since the sequence data suggest that perilipin A and B mRNAs arise by differential splicing of a common precursor, it seemed possible that the 3.9 kb mRNA contained the unique regions from both A and B cDNAs and was an effective precursor to the 3.0 kb mRNA. A predicted structure for the 3.9 kb mRNA species is depicted in FIG. 9A. None of the perilipin B clones included complete 3'sequences. However, the organization of the 3.9 kb RNA species has been confirmed by reverse transcription-coupled polymerase chain reaction (RT-PCR) analyses of rat adipocyte RNA.

Figure 9B:
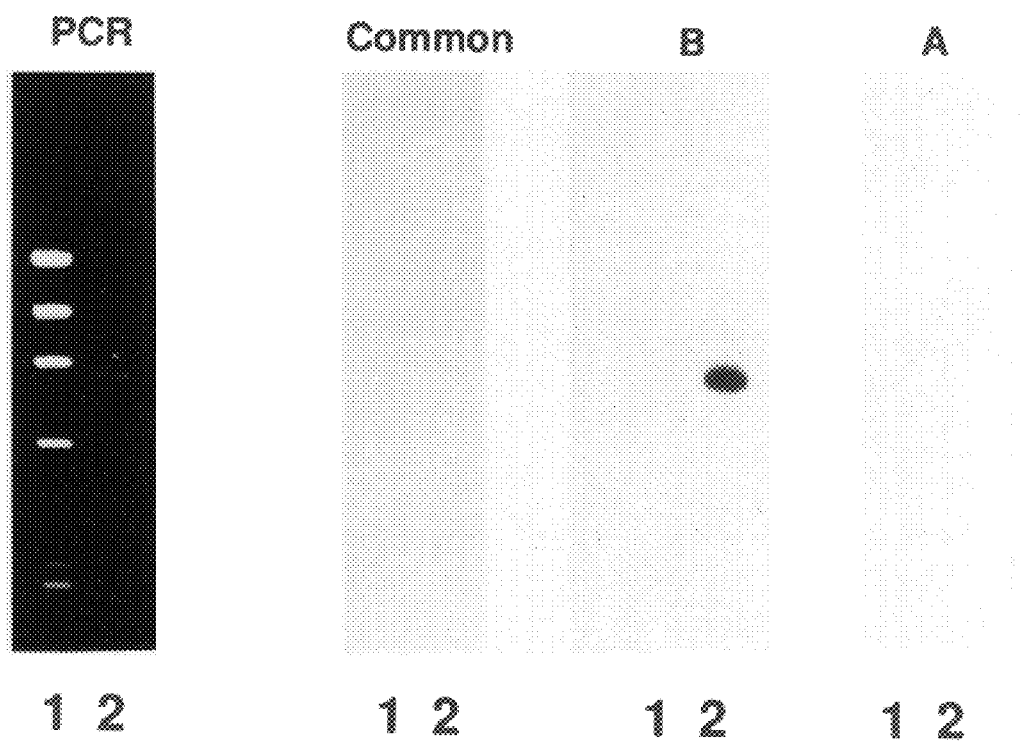

Rat primary adipocyte RNA was reverse transcribed using an oligonucleotide (i.e., oligo 1) located within the perilipin A cDNA and 3' to the presumptive acceptor splice junction (See, FIG. 9A). The resulting cDNA product was subjected to PCR using an additional oligonucleotide (i.e., oligo 2) located 3' to the donor splice junction but within perilipin B only (See, FIG. 9A). Under these conditions, only the 3.9 kb mRNA is predicted to yield an amplified product. No PCR fragment will be produced from the 3.0 kb mRNA. The reaction generated a single DNA fragment of approximately 0.8 kb that, as expected, hybridized with B sequences, but not with sequences common to both mRNAs nor with A sequences (See, FIG. 9B). The size of the fragment approximates the length difference between the two perilipin MRNA forms. The 3.9 kb mRNA encodes perilipin B, whereas the 3.0 kb mRNA encodes perilipin A.

Moreover, as with rat adipocytes, Northern analysis of mRNA extracted from murine adipocytes reveals that these adipocytes contain multiple perilipin mRNA. RNA was extracted from murine adipocytes by the RNAzol B (Cinna/Biotecx laboratories International, Inc., Friendswood, Tex.) and Northern analysis performed according to Wahl, et al. (*Meth. Enzymol.* 152:572–581)). The blots were probed with full length rat perilipin A cDNA. In doing so, the following four mRNA bands were observed: ~3.9 kb, ~3.0 kb, ~1.8 kb and ~1.5 kb (See, FIG. 10). In the murine adipocytes, both cultured and primary, the relative abundance of the message form is: 3.0>1.8≧3.9>1.5. The most abundant message, i.e., 3.0 kb, encodes perilipin A (~62-kDa), whereas the 3.9 kb message encodes perilipin B (~46-kDa). The translation product of the 1.8 kb message is expected to be the protein seen at ~47-kDa, infra., which is slightly larger than perilipin B. The translation product of the 1.5 kb message has yet to be identified in murine adipocytes, but a similar 1.5 kb message along with its translation product (~42-kDa) have been found in murine adrenal cortical cells (See, Example V, infra.).

The multiple perilipin mRNA forms found in murine adipocytes are consistent with the multiple perilipin proteins identified by Western analysis. Cultured murine 3T3-L1 adipocytes (ATCC # CCL 92.1 3T3-L1 (CL173), American Type Culture Collection, Rockville, Md.) were grown to confluence and harvested. Whole cell lysates were prepared for SDS-PAGE and Western blotting. Immunoaffinity purified antibodies prepared against full length rat perilipin A, as described above, recognize three protein bands in Western blots of whole adipocyte cell lysates. One major band that migrates as a ~62-kDa protein is perilipin A which, as expected, exhibits altered migration in SDS-PAGE (to ~65-kDa) when obtained from cells that had been stimulated. The second band migrates, slightly above perilipin B, as a protein of ~47-kDa. The third bands seen in the murine adipocyte Western blots corresponds to the ~46-kDa perilipin B of rat adipocytes. As previously mentioned, it should be noted that the translation product of the 1.5 kb message, supra., has yet to be identified in murine adipoyctes, but a similar 1.5 kb message along with its translation product (~42-kDa) have been found in murine adrenal cortical cells (See, Example V, infra.).

EXAMPLE V

Multiple Perilipin mRNA Forms in Adrenal Cells

Cultured Y-1 adrenal cortical cells (ATCC # CCL79 Y-1, American Type Culture Collection, Rockville, Md.) were grown to confluence and harvested. Whole cell lysates were prepared for SDS-PAGE and Western blotting. In some cases the cells were homogenized and centrifuged to yield three gross fractions: membrane pellets, aqueous supernates, and floating fat cakes. Immunoaffinity purified antibodies prepared against full length rat perilipin A, as described above, recognize two major and two minor protein bands in Western blots of whole adrenal cell lysates. One major band that migrates as a ~62-kDa protein is perilipin A which, as expected, exhibits altered migration in SDS-PAGE (to ~65-kDa) when obtained from cells that had been stimulated with either ACTH or forskolin, both of which elevate cAMP in these cells. The second major band migrates as a protein of ~42-kDa, and is equal in intensity in the Western blot to perilipin A. This smaller species is not apparent above the background staining in Western blots of adipocytes. This new protein is identified as perilipin C. Finally, one of the two minor bands seen in the adrenal Western blots corresponds to the ~46-kDa perilipin B of adipocytes, and the second minor band migrates slightly above perilipin B (~47-kDa). Thus, the cultured Y-1 adrenal cells contain a major form of perilipin (~42-kDa) and a minor form (~47-kDa) which are either present in relatively low abundance or absent from rat adipocytes.

The floating fat cakes of adrenal homogenates are comprised of the lipid droplets containing the cholesteryl ester precursors of steroid synthesis. All of the forms of perilipin described above migrate predominantly, if not exclusively, with the lipid cakes of centrifuged homogenates; only minor amounts of these proteins are found the supernate or membrane pellet fractions. In this respect, the adrenal perilipins behave as do the adipocyte proteins.

In addition to the finding that adrenal cells contain perilipins, the detection of a major form, perilipin C (~42-kDa) in the adrenal cells is of particular interest. A further finding is that this species does not exhibit altered migration in SDS-PAGE when obtained from cells that had been stimulated with either ACTH or forskoln. Such data suggest that perilipin C differs in its carboxyl-terminal region from perilipin A, wherein are found the A-kinase phosphorylation sites responsible for the shift in SDS-PAGE migration. This speculation is supported by the failure of antibodies immunoaffinity purified against the carboxyl-terminal portion unique to perilipin A to recognize perilipin C.

Northern analysis of mRNA extracted from Y-1 adrenal cells provides further evidence that the proteins identified by the Western analysis are perilipins and that the relative abundance of these forms differs in adrenal and adipose cells. RNA was extracted from Y-1 adrenal cells by the RNAzol B (Cinna/Biotecx Laboratories International, Inc., Friendswood, Tex.) and Northern analysis performed according to Wahl, et al. (*Meth. Enzymol.* 152:572–581)). The blots were probed with full length rat perilipin A cDNA.

Four mRNA bands were observed, two major (~3.0 kb and 1.5 kb) and two minor (~3.9 kb and ~1.8 kb). The relative abundance of the four message forms is: $1.5 \geq 3.0 >> 3.9 = 1.8$. The 3.0 kb and 3.9 kb mRNAs encode perilipin A and perilipin B, respectively. It is expected that the major 1.5 kb mRNA species represents the new major perilipin protein (i.e., perilipin C, 42-kDa) discussed above. Similarly, it is expected that the 1.8 kb mRNA encodes the protein noted above that migrates at approximately ~47-kDa. It is noted that the above four messages (i.e., ~3.0 kb, ~1.8 kb, ~3.9 kb and ~1.5 kb) are found in cultured murine 3T3-L1 adipocytes (ATTC # CCL 92.1 3T3-L1 (CL 173), American Type Culture Collection) as well as in primary murine adipocytes (See, FIG. 10). However, in the murine adipocytes, the two major forms are the 3.0 kb and 1.8 kb messages. The 1.5 kb mRNA, which is a major species in adrenals, is a minor species in murine adipocytes.

EXAMPLE VI

Tissue and Developmental Specificity of Perilipin mRNA Expression

The complex pattern of perilipin mRNA organization prompted an examination of tissue specificity by RNA blot hybridization. The autoradiogram of the RNA blot was deliberately overexposed in order to detect potential faint hybridization of perilipin probes to RNA isolated from other rat tissues. The 3.9 kb and 3.0 kb perilipin mRNAs were not detected by RNA blot hybridization in any of the following tissues: brain, heart, kidney, liver, lung, muscle, stomach and testes. If perilipin mRNA is present in these non-adipose tissues, it cannot represent more than 0.002% of total mRNA.

Although perilipin mRNA was not found in the above tissues, it has been found in adrenal cells derived from the adrenal cortex. More particularly, it has been discovered that murine adrenal cortical cells contain lipid droplet-associated proteins that correspond, both by Western and Northern analysis, to the perilipins found in adipocytes. Moreover, as with the adipocytes, multiple perilipin mRNA forms have been found in the adrenal cells. See, Example V, supra. It should be noted, however, that the abundance of perilipin in adrenal cortical cells is approximately 2 to 5 percent of that found in adipocytes; this is true for both mRNA abundance and protein abundance.

Although perilipin has been found in adrenal cells, it is expressed to a far greater extent in adipocytes. As such, expression of perilipin during adipocyte differentiation in a tissue culture model system was examined. RNA, prepared from 3T3-L1 murine pre-adipocytes and differentiated adipocytes, was hybridized on blots with a probe containing sequences common to rat perilipin A and B. Perilipin mRNA was detected only after adipocyte differentiation was initiated and, as in rat adipocytes, the differentiated 3T3-L1 cells express multiple mRNA forms (FIG. 10).

EXAMPLE VII

Correlation Between Appearance of Perilipin MRNA and Lipid Accumulation in Cultured Adipocytes FIG. 11 compares time-course of appearance of perilipin mRNA and triacylglycerol accumulation in differentiating 3T3-L1 adipocytes in culture. 3T3-L1 fibroblasts (ATCC # CCL 92.1 3T3-L1 (CL 173), American Type Culture Collection, Rockville, Md.) were stimulated to differentiate into adipocytes according to Rubin, et al. (*J. Biol. Chem.* 253:7570 (1978)). Triacylglycerol was assayed colorimetrically with the Sigma Kit #405. Northern blotting was performed according to Wahl, et al. (*Meth. Enzymol.* 152:572–581(1987)) with probes constructed from the cDNA sequence for the gene encoding rat perilipin A (Sequence I.D. No. 1). Perilipin mRNA appeared at day 3 concurrent with the appearance of lipid, and the message increased progressively in concert with lipid accumulation over the next week in culture. Moreover, it was found by immunocytochemical studies at the electron microscopic level that perilipin resides in close proximity to the surface of the lipid in 3T3-L1 adipocytes. If not in direct contact with the lipid, the protein is probably not more than one phospholipid monolayer away from the lipid.

---

What is claimed is:

1. An isolated nucleic acid sequence that encodes a human perilipin protein, wherein said perilipin protein comprises an amino acid sequence as set forth in SEQ ID NO:6.

2. The isolated nucleic acid sequence of claim 1 wherein said nucleic acid sequence comprises a sequence as set forth in SEQ ID NO:5.

3. The isolated nucleic acid sequence of claim 1 wherein said nucleic acid sequence selectively hybridizes to a polynucleotide comprising residues 859 to 1265 of the nucleotide sequence of SEQ ID NO:5.

4. An isolated nucleic acid sequence that encodes a perilipin protein comprising an amino acid sequence selected from the group consisting of SEQ ID NO:2 and SEQ ID NO:4.

5. The isolated nucleic acid sequence of claim 4 wherein said nucleic acid sequence encodes a perilipin protein comprising the amino acid sequence of SEQ ID NO:2.

6. The isolated nucleic acid sequence of claim 4 wherein said nucleic acid sequence encodes a perilipin protein comprising the amino acid sequence of SEQ ID NO:4.

7. A recombinant expression vector that comprises a DNA sequence that encodes a perilipin protein selected from the group consisting of a perilipin protein comprising an amino acid sequence selected from the group consisting of SEQ ID NO:2, SEQ ID NO:4 and SEQ ID NO:6, wherein said DNA sequence is operably linked to an expression control sequence.

8. The recombinant expression vector of claim 7 wherein said vector replicates in a prokaryotic organism.

9. The recombinant expression vector of claim 7 wherein said vector replicates in an eukaryotic organism.

10. A method for producing a substantially pure perilipin protein, said method comprising:

(a) transfecting a culture of cells with a recombinant expression vector of claim 7;

(b) growing the transfected cells of step (a) such that perilipin protein is expressed; and (c) recovering said perilipin protein.

11. The method of claim 10 wherein said DNA sequence encodes a perilipin protein having an amino acid sequence selected from the group consisting of SEQ ID NO:2 and SEQ ID NO:4.

12. The method of claim 10 wherein said DNA sequence encodes a perilipin protein having an amino acid sequence comprising SEQ ID NO:6.

13. The method claim 10 wherein said recombinant expression vector replicates in a prokaryotic organism.

14. The method of claim 10 wherein said recombinant expression vector replicates in a eukaryotic organisms.

* * * * *